US007582680B1

(12) United States Patent  (10) Patent No.: US 7,582,680 B1
Shi et al.                  (45) Date of Patent:    *Sep. 1, 2009

(54) METHODS AND COMPOSITIONS FOR TREATING MAMMALIAN SPINAL CORD INJURIES

(75) Inventors: Riyi Shi, West Lafayette, IN (US);
Richard B. Borgens, Delphi, IN (US)

(73) Assignees: Purdue Research Foundation, West Lafayette, IN (US); The United States of America as represented by the Secretary of the Army, Washington, DC (US); National Science Foundation, Arlington, VA (US)

( * ) Notice: Subject to any disclaimer, the term of this patent is extended or adjusted under 35 U.S.C. 154(b) by 894 days.

This patent is subject to a terminal disclaimer.

(21) Appl. No.: 09/438,206

(22) Filed: Nov. 12, 1999

Related U.S. Application Data

(60) Provisional application No. 60/108,145, filed on Nov. 12, 1998.

(51) Int. Cl.
*A61K 31/08* (2006.01)
*A61K 31/44* (2006.01)
(52) U.S. Cl. .......................... 514/723; 514/352
(58) Field of Classification Search ............. 514/723, 514/352
See application file for complete search history.

(56) References Cited

U.S. PATENT DOCUMENTS

| 4,369,769 | A | * | 1/1983 | Edwards ............ 606/61 |
| 4,599,354 | A | * | 7/1986 | Shulman ............ 514/530 |
| 4,919,140 | A | | 4/1990 | Borgens et al. |
| 5,382,584 | A | * | 1/1995 | Balasubramanian |
| 5,470,568 | A | | 11/1995 | Lee |
| 5,545,648 | A | | 8/1996 | Hansebout et al. |
| 5,605,687 | A | | 2/1997 | Lee |
| 6,090,823 | A | * | 7/2000 | Ishikawa |
| 6,432,434 | B1 | | 8/2002 | Meyerhoff et al. |
| 6,440,455 | B1 | | 8/2002 | Benowitz |
| 6,495,532 | B1 | | 12/2002 | Bathurst et al. |
| 2003/0118545 | A1 | | 6/2003 | Shi et al. |
| 2004/0214790 | A1 | | 10/2004 | Borgens |

FOREIGN PATENT DOCUMENTS

| EP | 0 484 186 A1 | 5/1992 |
| EP | 0 484 186 B1 | 12/1999 |
| WO | WO-97/35577 | * 10/1997 |
| WO | WO 02/092107 | 11/2002 |
| WO | WO 2004/060146 A2 | 7/2004 |

OTHER PUBLICATIONS

Potter PJ, "4-aminopyridine: Six years experience and progress in spinal cord injury" Clin Invest Med 19(4), 1996: Suppl. S80, #533.*

(Continued)

*Primary Examiner*—San-ming Hui
(74) *Attorney, Agent, or Firm*—Mueting Raasch & Gebhardt, P.A.

(57) ABSTRACT

Methods of treating an injured vertebrate spinal cord are described. In one aspect of the invention, a method of treating an injured vertebrate spinal cord includes contacting the spinal cord with a biomembrane fusion agent such as a polyalkylene glycol, especially polyethylene glycol. In alternative embodiments of the invention, methods of treating an injured vertebrate spinal cord include contacting the cord with a biomembrane fusion agent and a potassium channel blocker. Other aspects of the invention include compositions for treating a vertebrate nervous system. A preferred composition includes a biomembrane fusion agent, such as a polyalkylene glycol, and a potassium channel blocker, such as an amino-substituted pyridine.

14 Claims, 14 Drawing Sheets

OTHER PUBLICATIONS

Davis et al., Journal of Spinal Disorders, 1990;3(4):299-306.*
Product information of Depo-Medrol from PDR 1996, p. 2600-2602.*
Brown, Clinical Orthopedics and Related Research, 1977;129:72-78.*
Merck Manual of Medical Information—Home Edition, 1997, p. 352-353.*
Ducker et al., J. Neurosurg., 1969;30(6):693-697.*
Bittner, George D. et al., "Reconnection Of Severed Nerve Axons With Polyethylene Glycol" *Brain Research*, vol. 367, 1986:351-355.
Krause, Todd L. and George D. Bittner, "Rapid Morphological Fusion Of Severed Myelinated Axons By Polyethylene Glycol" *Proc. Natl. Acad. Sci. USA*, vol. 87, 1990: 1471-1475.
Krause, Todd L. et al., "Rapid Artificial Restoration Of Electrical Continuity Across A Crush Lesion Of A Giant Axon" *Brain Research*, vol. 561, 1991: 350-353.
Pratt, Kimball et al., "Plasma And Cerebrospinal Fluid Concentrations Of 4-Aminopyridine Following Intravenous Injection And Metered Intrathecal Delivery in Canines" *Journal of Neurotrauma*, vol. 12, 1995: 23-39.
Shi, R. and A. R. Blight, "Differential Effects Of Low And High Concentrations Of 4-Aminopyridine On Axonal Conduction In Normal And Injured Spinal Cord", *Neuroscience*, vol. 77, 1997: 553-562.
Blight, Andrew R., "Effect Of 4-Aminopyridine On Axonal Conduction-Block In Chronic Spinal Cord Injury", *Brain Research Bulletin*, vol. 22, 1989: 47-52.
Blight, Andrew R. et al., "Cutaneus Trunci Muscle Reflex Of The Guinea Pig", *The Journal of Comparative Neurology*, vol. 296, 1990: 614-633.
Shi, Riyi et al., "Conduction Block In Acute And Chronic Spinal Cord Injury: Different Dose-Response Characteristics For Reversal By 4-Aminopyridine", *Experimental Neurology*, vol. 148, 1997: 495-501.
Shi, Ri-Yi et al., "Calcium Antagonists Fail To Protect Mammalian Spinal Neurons After Physical Injury", *Journal of Neurotrauma*, vol. 6, 1989: 261-275.
Lee, Raphael C. et al., "Surfactant-Induced Sealing Of Electropermeabilized Skeletal Muscle Membranes In Vivo", *Proc. Natl. Acad. Sci. USA*, vol. 89, 1992: 4524-4528.
Borgens, Richard B. et al., "Axonal Regeneration In Spinal Cord Injury: A Perspective And New Technique", *Journal of Comparative Neurology*, vol. 250, 1986: 157-167.
Blight, Andrew R., "Morphometric Analysis Of A Model Of Spinal Cord Injury In Guinea Pigs, With Behavioral Evidence Of Delayed Secondary Pathology" *Journal of the Neurological Sciences*, vol. 103, 1991: 156-171.
Shi, Riyi et al., "Functional Reconnection Of Severed Mammalian Spinal Cord Axons With Polyethylene Glycol", *Journal of Neurotrauma*, vol. 16, 1999: 727-738.
Shi, Riyi and Richard B. Borgens, "Acute Repair Of Crushed Guinea Pig Spinal Cord By Polyethylene Glycol", *J. Neurophysiol*, vol. 81, 1999: 2406-2414.
Benzon et al. "The Effect of Polyethylene Glycol on Mammalian Nerve Impulses" *Anesth. Analg.* 1987;66:553-9.
Borgens et al. "A subcutaneous tri-block copolymer produces recovery from spinal cord injury" *J. Neurosci. Res.* 2004;76:141-154.
Carpenter et al. "Response of dogs to repeated intravenous injection of polyethylene glycol 4000 with notes on excretion and sensitization." *Toxicol. Appl. Pharmacol.* 1971;18:35-40.
Hansen et al. "A pathological-anatomical study on disk degeneration in dog with special reference to the so-called enchondrosis intervertebralis" *Acta Orth Scand* 1952;11:1-129.
Horelein, B.F. "Comparative disk disease: man and dog." *JAAHA* 1979;15:535-545.
Luo et al. "Polyethylene glycol immediately repairs neuronal membranes and inhibits free radical production after acute spinal cord injury" *J. Neurochemistry* 2002;83:471-480.
Maskarinec et al. "Direct observation of poloxamer 188 insertion into lipid monolayers" *Biophys. J.* 2002;82:1453-1459.

McNally et al. "Three-Dimensional Imaging of Living and Dying Neurons with Atomic Force Microscopy" *J. Neurocytology* 2004;33:251-258.
Pointillart et al. "Pharmacological therapy of spinal cord injury during the acute phase" *Spinal Cord* 2000;38:71-76.
Principe, A.H. "Polyethylene glycols. Studies of absorption, excretion, retention, and identification" *J. Forensic Sci.* 1968;13:90-113.
Selby, R. *Neurosurgery* "Correspondence" 1983;12:5:591.
Shaffer et al. "The absorption and excretion of the solid polyethylene glycols" ("Carbowax" Compounds). *J. Amer. Pharm. Assoc.* 1947;36:152-157.
Shaffer et al. "Renal excretion and volume distribution of some polyethylene glycols in the dog." *Amer. J. Of Phys.* 1948;152:93-99.
Short et al. "High dose methylprednisolone is the management of acute spinal cord injury- a systematic review from a clinical perspective" *Spinal Cord* 2000;38:273-286.
Smyth et al. "The toxicity of high molecular weight polyethylene glycols; chronic oral and parenteral administration." *J. Amer. Pharm. Assoc.* 1947;36:157-160.
Working et al. Safety of poly (ethylene glycol) and poly (ethylene glycol) derivatives in Poly (ethylene glycol) chemistry and biological applications. Harris and Zalipsky (eds.), in *Polyethylene glycol): Chemistry and Biological Applications* 1997;Title page, Table of Contents, and pp. 45-57.
Laverty et al. "A Preliminary Study of Intravenous Surfactants in Paraplegic Dogs: Polymer Therapy in Canine Clinical SCI" *J. of Neurotrauma* 2004;21:1767-1777.
Borgens et al., "Immediate recovery from spinal cord injury through molecular repair of nerve membranes with polyethylene glycol," in FASEB, vol. 14, 27-35, Jan. 2000.
Koob et al. "Intravenous Polyethylene Glycol Inhibits The Loss of Cerebral Cells after Brain Injury" *J Neurotrauma*, Oct. 2005;22(10):1092-111.
Altizer et al. "Endogenous electric current is associated with normal development of the vertebrate limb" *Developmental Dynamics* 2001;221(4):391-401.
Borgens, "Acute Repair of Spinal Injury with Fusogens" Grant Abstract, Grant No. 5R01NS039288-01A1 [online] National Institute of Neurological Disorders and Stroke Project dates Jun. 1, 2000-Feb. 28, 2003. [retrieved on Feb. 23, 2004]. Retrieved from the Internet: URL:http://crisp.cit.nih.gov/crisp/CRISP_LIB.getdoc?textkey=6193809&p_grant_num=1R01N.
Borgens, "Acute Repair of Spinal Injury with Fusogens" Grant Abstract, Grant No. 5R01NS039288-01A1S1 [online] National Institute of Neurological Disorders and Stroke Project dates Jun. 1, 2000-Feb. 28, 2003. [retrieved on Feb. 28, 2004]. Retrieved from the Internet: URL:http://crisp.cit.nih.gov/crisp/CRISP_LIB.getdoc?textkey=6401733&p_grant_num=3R01N.
Borgens, "Restoring Function of the Injured Human Spinal Cord" (Advances in Anatomy, Embryology and Cell Biology, 171) Title Page and Table of Contents Only, 1997.
Center for Paralysis Research, Purdue University, Institute for Applied Neurology, *Synapses*, Summer 2003. 4 pages.
Duerstock et al. "A comparative study of the quantitative accuracy of three-dimensional reconstructions of spinal cord from serial histological section" *J. of Microscopy* 2003; 210(Pt. 2):138-148.
Moriarty et al. "An oscillating extracellular voltage gradient reduces the density and influences the orientation astrocytes in injured mammalian spinal cord" *J. Neurocytol* 2001;30(1):45-57.
Potter PJ, "Sustained improvements in neurological function in spinal cord injured patients treated with oral 4-aminopyridine: three cases" *Spinal Cord* 1998;36:147-155.
Qiao et al. "Effects of 4-aminopyridine on motor evoked potentials in patients with spinal cord injury" *J Neurotrauma* 1997;14(3):135-49.
Adams-Graves et al., "RheothRx (poloxamer 188) injection for the acute painful episode of sickle cell disease: a pilot study," *Blood*, Sep. 1, 1997; 90(5):2041-6.
Ahkong et al., "Movements of fluorescent probes in the mechanism of cell fusion induced by poly(ethylene glycol)," *J. Cell Sci.*, 1987; 88:389-98.
Aldewinckel et al., "Effects of Poly (Ethylene Glycol) on Liposomes and Erythrocytes permeability changes and membrane fusion," *Biochim. Biophys. Acta.*, 1982; 689:548-560.

Allen, "Surgery of experimental lesion of spinal cord equivalent to crush injury of fracture dislocation of spinal column," *J. Am. Med. Assoc.*, Sep. 9, 1911; 57:878-880.

Anderson et al., "Characteristics of intraspinal grafts and locomotor function after spinal cord injury," *Proceedings of the Third Altschul Symposium on Neural Cell Specification: Molecular Mechanisms and Neurotherapeutic Implications*, Juurlink et al., eds., Plenum Press, New York, 1995; 249-266.

Anderson et al., "Regeneration of spinal neurons in inflammammalian vetebrates: morphological and developmental aspects," *J. Hirnforsch.*, 1983; 24:371-398.

Armstrong et al., "Inhibition of red blood cell-inducted platelet aggregation in whole blood by a nonionic surfactant, poloxamer 188 (RheothRx® injection)," *Thrombosis Research*, 1995; 79(5/6):437-50.

Asano et al., "Horseradish peroxidase used to examine the distribution of axonal damage in spinal cord compression injury in vitro," *J. Neurotrauma*, 1995; 12:993 (Abst. No. TS2).

Basso et al., "A Sensitive and reliable locomotor rating scale for open field testing in rats," *J. Neurotrauma*, 1995; 12(1):1-21.

Benzel, *Spine Surgery: Techniques, Complication Avoidance and Management*, Philadelphia, PA 1999; cover page, title pages, table of contents and 369-387 and 389-400.

Berne et al. eds., "Generation and Conduction of Action Potentials," *Physiology*, 3rd Edition, Mosby, St. Louis, MO, 1993; 36-54.

Bernstein et al., "Spinal cord regeneration: synaptic renewal and neurochemistry," *Neuronal Plasticity*, Cotman, ed., Raven Press, New York, 1978; 49-71.

Bernstein et al., "Synaptic frequency alteration on rat ventral horn neurons in the first segment proximal to spinal cord hemisection: an ultrastructural statistical study of regenerative capacity," *J. Neurocytol.*, 1977; 6:85-102.

Bernstein et al., "Synaptic reorganization following regeneration of goldfish spinal cord," *Exp. Neurol.*, 1973; 41:402-410.

Berry, "Chapter 4: Regeneration in the central nervous system," *Recent Advances in Neuropathology*, Smith et al., eds., Churchill Livingstone, New York, 1979; 67-111.

Bisby, "Regeneration of peripheral nervous system axons," *The Axon Book*, Waxman et al., eds., Oxford UP, New York, 1995, 553-578.

Bittner, "Long-term survival of anucleate axons and its implications for nerve regeneration," *TINS*, 1991; 14(5):188-193.

Blight, "Delayed demyelination and macrophage invasion: A candidate for secondary cell damage in spinal cord injury," *Central Nervous System Trauma*, 1985; 2(4):299-315.

Blight et al., "The effects of 4-aminopyridine on neurological deficits in chronic cases of traumatic spinal cord injury in dogs: a phase I clinical trial," *J. Neurotrauma*, 1991; 8(2):103-119.

Blight et al., "Morphometric analysis of experimental spinal cord injury in the cat: the relation of injury intensity to survival of myelinated axons," *Neuroscience*, 1986; 19(1):321-341.

Blight, "Remyelination, Revascularation, and Recovery of Function in Experimental Spinal Cord Injury," Seil, ed., *Advances in Neurobiology: Neural Injury and Regeneration*, Raven Press, New York, 1993; 59, 91-104.

Borgens, "Acute Repair of Spinal Injury with Fusogens" Grant Abstract, Grant No. 5R01NS39288-02 [online] National Institute of Neurological Disorders and Stroke. 2001. [retrieved on Feb. 8, 2003]. Retrieved from Dialog.

Borgens, "Acute Repair of Spinal Injury with Fusogens" Grant Abstract, Grant No. 5R01NS039288-03 [online] National Institute of Neurological Disorders and Stroke Project dates Jun. 1, 2000-Feb. 28, 2003. [retrieved on Feb. 8, 2003]. Retrieved from the Internet: URL:http://commons.cit.nih.gov/crisp3/crisp_lib.getdoc?textkey=6531108&p_grant_num=5R.

Borgens, "Acute Treatment of Contusion Injury to the Spinal Cord," Grant Abstract, Grant No. DHHS-R49-CCR-503590-03. (Jun. 16, 1993) [online]. National Center for Injury Prevention and Control [retrieved on Feb. 8, 2003]. Retrieved from Dialog.

Borgens, "Acute Treatment of Spinal Trauma by Electrical Fields" Final Report PHS: CDC/CIC#R49/CCR509137. NTIS Item No. PB98155849 (1998) 168 pages.

Borgens, "Chapter 5: Applied Voltages in Spinal Cord Reconstruction: History, Strategies and Behavioural Models," *Spinal Cord Dysfunction III: Functional Stimulation*, Illis, ed., Oxford UP 1992, 110-144.

Borgens et al., "Behavioral recovery induced by applied electric fields after spinal cord hemisection in guinea pig," *Science*, Oct. 16, 1987; 238:366-369.

Borgens et al., "Behavioral recovery from spinal cord injury following delayed application of polyethylene glycol," *J. Exp. Biol.*, 2002; 205:1-12.

Borgens, "Concept and Innovation: Cellular Engineering: Molecular Repair of Membranes to Rescue Cells of the Damaged Nervous System," *Neurosurgery*, Aug. 2001; 49(2):370-379.

Borgens et al., "Delayed application of direct current fields in experimental spinal cord injuries," *J. Rest. Neurol. Neurosci.*, 1993; 5(5):173-179.

Borgens et al., "Effects of applied electric fields on clinical cases of complete paraplegia in dogs," *J. Rest. Neurol. Neurosci.*, 1993; 5:305-322.

Borgens, Richard B., "Electronic Facilitation of Functional Recovery Following CNS Trauma," Grant Abstract, Grant No. 9631560 [online]. National Science Foundation, Sep. 15, 1996 to Aug. 31, 1999 [retrieved on Oct. 12, 2002]. Retrieved from the Internet:<URL:https://www.fastlane.nsf.gov/servlet/showaward?award=9631560>; 2 pgs.

Borgens, "Electrically Mediated Trauma Repair" Grant Abstract, Grant No. DAMD17-94-J-4242 [online] Project dates Aug. 22, 1994-Aug. 21, 1998). [retrieved on Feb. 8, 2003]. Retrieved from Dialog.

Borgens, Richard B. Electrically Mediated Trauma Repair. Grant No. DAMD17-94-J-4242. Final Report. NTIS Item No. ADA 359272. Sep. 1998. 139 pages.

Borgens et al., "Functional recovery after spinal cord hemisection in guinea pigs: The effects of applied electrical fields," *J. Comp. Neurol.*, 1990; 296:634-653.

Borgens et al., "Immediate recovery from spinal cord injury through molecular repair of nerve membranes with polyethylene glycol," *FASEB J.*, Jan. 2000; 14(1):27-35.

Borgens et al., "An Imposed Oscillating Electrical Field Improves the Recovery of Function in Neurologically Complete Paraplegic Dogs," *J. Neurotrauma*, Nov. 7, 1999; 16:639-657.

Borgens et al., "Large and persistent electrical currents enter the transected lamprey spinal cord," *Proc. Natl. Acad. Sci. U.S.A.*, Feb. 1980; 77(2):1209-1231.

Borgens et al., "Rapid Recovery from Spinal Cord Injury After Subcutaneously Administered Polyethylene Glycol," *J. Neurosci. Res.*, 2001; 66:1179-1186.

Borgens et al., "The Responses of Mammalian Spinal Axons to an Applied DC Voltage Gradient," *Exp. Neurol.*, Jun. 1997; 145(2):376-389.

Borgens et al., "Transected dorsal column axons within the guinea pig spinal cord regenerate in the presence of an applied electric field," *J. Comp. Neurol.*, 1986; 250:168-180.

Borgens, "Voltage Gradients and Ionic Currents in Injured and Regenerating Axons," *Advances in Neurology, vol. 47: Functional Recovery in Neurological Disease*, Waxman, ed., 1988, Raven Press, New York, 51-66.

Bracken et al., "A randomized, controlled trial of methylprednisolone or naloxone in the treatment of acute spinal-cord injury: Results of the Second National Acute Spinal Cord Injury Study," *New Eng. J. Med.*, May 17, 1990; 322(20):1405-1411.

Bracken et al., "Efficacy of methylprednisolone in acute spinal cord injury," *JAMA*, Jan. 6, 1984; 251(1):45-52.

Bregman et al., "Chapter 26: Intervention strategies to enhance anatomical plasticity and recovery of function after spinal cord injury," *Adv. Neurol.*, Seil, ed., 1997; 72:257-275.

Bregman et al., "Recovery of function after spinal cord injury: Mechanisms underlying transplant-mediated recovery of function differ after spinal cord injury in newborn and adult rats," *Exp. Neurol.*, Sep. 1993; 123(1):3-16.

Bregman et al., "Recovery from spinal cord injury mediated by antibodies to neurite growth inhibitors," *Nature*, Nov. 30, 1995; 378:498-501.

Bregman et al., "Transplants, neruotrophic factors and myelin-associated neurite growth inhibitors: Effects on recovery of locomotor function after spinal cord injury in adult rats," *Soc. Neurosci. Abst.*, 1996; 22:764.

Cajal, "Degeneration and regeneration of the nervous system," May, Trans. and Ed., Oxford UP, London, 1928; Cover pg., Publication pg., and Table of Contents only. (15 pgs.).

Carafoli et al., *Calcium ions and mitochondria, Symposium of the Society for Experimental Biology: Calcium and Biological Systems*, vol. 30, Cambridge UP, New York, 1976, 89-115.

Carafoli et al., "The Calcium Signal," *Sci. Am.*, Nov. 1985; 253:70-78.

Carr Jr. et al., "Effects of poloxamer 188 on the assembly, structure and dissolution of fibrin clots," *Thrombosis & Haemostasis*, 1991; 66(5):565-8.

Center for Paralysis Research, Purdue University, Institute for Applied Neurology, *Synapses*, Fall 2002. 5 pages.

Center for Paraylsis Research, Purdue University, Institute for Applied Neurology, *Synapses*, Spring 2002. 4 pages.

Center for Paralysis Research, Purdue University, Institute for Applied Neurology, *Synapses*, Fall 2001. 4 pages.

Center for Paralysis Research, Purdue University, Institute for Applied Neurology, *Synapses*, Fall 2000. 4 pages.

Center for Paralysis Research, Purdue University, Institute for Applied Neurology, *Synapses*, Spring 2000. 4 pages.

Cheng et al., "Gait Analysis of Adult Paraplegic Rats after Spinal Cord Repair," *Exp. Neurol.*, Dec. 1997; 148(2):544-557.

Chernoff et al., "Review: Developmental aspects of spinal cord and limb regeneration," *Develop. Growth Differ.*, Apr. 1995; 37(2):133-147.

Choi, "Glutamate neurotoxicity and diseases of the nervous system," *Neuron*, 1988; 1:623-634.

Choi et al., "The role of glutamate neurotoxicity in hypoxic-ischemic neuronal death," *Ann. Rev. Neurosci.*, 1990; 13:171-182.

Coates et al., "Clinicopathologic Effects of a 21-Aminosteroid Compound (U74389G) and High-Dose Methylprednisolone on Spinal Cord Function After Simulated Spinal Cord Trauma," *Veterinary Surgery*, 1995; 24(2):128-139.

Coates, "Intervertebral Disk Disease," *Common Neurological Problems*, Jan. 2000; 30(1):77-110.

Davidson et al., "Improved techniques for the induction of mammalian cell hybridization by polyethylene glycol," *Somat. Cell Genet.*, 1976; 2(2):165-176.

Davidson et al., "Polyethylene Glycol-Induced Mammalian Cell Hybridization: Effect of Polyethylene Glycol Molecular Weight and Concentration," *Somat. Cell Genet.*, 1976; 2:271-280.

Donaldson et al., "Experimental Studies: Polyethylene Glycol Rapidly Restores Physiological Functions in Damaged Sciatic Nerves of Guinea Pigs," *Neurosurgery*, Jan. 2002; 50(1):147-157.

Duerstock et al., "Advances in three-dimensional reconstruction of the experimental spinal cord injury," *Computer Medical Imaging and Graphics*, 2000; 24:389-406.Feb. 26, 2003.

Duerstock et al., "Three-dimensional morphometry of spinal cord injury following polyethylene glycol treatment," *J. Exper. Biol.*, 2002; 205:13-24.

Eidelberg et al., "Relationship between residual hindlimb-assisted locomotion and surviving axons after incomplete spinal cord injuries," *Exp. Neurol.*, Aug. 1977;56(2):312-322.

Eidelberg et al., "Locomotor control in macaque monkeys," *Brain*, Dec. 1981; 104(IV):647-663.

Farooqui et al., "Excitatory amino acid receptors, neural membrane phospholipid metabolism and neurological disorders," *Brain Res. Rev.*, 1991; 16:171-191.

Fawcett et al., "Peripheral nerve regeneration," *Annu. Rev. Neurosci.*, 1990; 13:43-60.

Fehlings et al., "The relationships among the severity of spinal cord injury, residual neurological function, axon counts, and counts of retrogradely labeled neurons after experimental spinal cord injury," *Exp. Neurol.*, 1995; 132:220-228.

Follis et al., "Role of poloxamer 188 during recovery from ischemic spinal cord injury: a preliminary study," *Journal of Investigative Surgery*, 1996; 9:149-56.

Frim et al., "Effects of biologically delivered NFG, BDNF and bFGF on straital excitotoxic lesions," *NeuroReport*, Apr. 1993; 4(4):367-70.

Frim et al., "Implanted NFG-producing fibroblasts induce catalase and modify ATP levels but do not affect glutamate receptor binding or NMDA receptor expression in the rat straitum," *Experimental Neurology*, Aug. 1994; 128(2):172-80.

Frim et al., "Local protective effects of nerve growth factor-secreting fibroblasts against excitotoxic lesions in the rat striatum," *Journal of Neurosurgery*, Feb. 1993; 78(2):267-73.

Frim et al., "NGF reduces straital excitotoxic neuronal loss without affecting concurrent neuronal stress," *NeuroReport*, Jun. 1993; 4(6):655-8.

Geisler et al., "Recovery of motor function after spinal-cord-injury—a randomized, placebo-controlled trial with GM-1 ganglioside," *The New England Journal of Medicine*, Jun. 27, 1991; 324(26):1829-1838.

Griffin et al., "Axonal degeneration and disorders of the axonal cytoskeleton," *The Axon*, Waxman et al., eds., New York, Oxford UP, 1995, 375-390.

Hall et al., "Central nervous system trauma and stroke, II: Physiological and pharmacological evidence for involvement of oxygen radicals and lipid peroxidation," *Free Rad. Biol. Med.*, 1989; 6(3):303-313.

Hall, "Inhibition of lipid peroxidation in CNS trauma," *J. Neurotrama*, 1991; 8(Suppl. 1):S-31-S-40.

Hall, "The neuroprotective pharmacology of metholprednisolone," *J. Neurosorg*, Jan. 1992; 76(1):13-22.

Hall et al., "U-78517F: A potent inhibitor of lipid peroxidation with activity in experimental brain injury and ischemia," *J. Pharm. Exp. Therap.*, 1991; 258(2):688-694.

Hannig et al., "Poloxamine 1107 sealing of radiopermeabilized erythrocyte membranes," *Int. J. Rad. Biol.*, 1999; 75(3):379-85.

Hansebout et al., "4-Aminopyridine in chronic spinal cord injury: A controlled, double-blind, crossover study in eight patients," *J. Neurotrauma*, 1993; 10(1):1-18.

Honmou et al., "Traumatic injury to the spinal axons," *The Axon*, Waxman et al., eds., Oxford UP, New York,1995, 480-503.

Jaeger et al., "Grafting in acute spinal cord injury: Morphological and immunological aspects of transplanted adult rat enteric ganglia," *Neuroscience*, 1993; 52(2):333-346.

Jewell et al., "Pharmacokinetics of RheothRx injection in healthy male volunteers," *Journal of Pharmaceutical Sciences*, Jul. 1997; 86(7):808-12.

Katayama et al., "Massive increases in extracellular potassium and the indiscriminate release of glutamate following concussive injury," *J. Neurosurg.*, Dec. 1990; 73(6):889-900.

Ketchum, "Peripheral Nerve Repair," *Fundamentals of Wound Management*, Hunt et al., eds., Appleton-Century-Crofts, New York, 1979; 459-475.

Kiernan, "Hypotheses concerned with axonal regeneration in the mammalian nervous system," *Biol. Rev.*, 1979, 54:155-197.

Kohmura et al., "Hippocampal neurons become more vulnerable to glutamate after subcritical hypoxia: an in vitro study," *J. Cereb. Blood Flow Metab.*, Nov. 1990; 10(6):877-884.

Lee et al., "The changing landscape of ischaemic brain injury mechanisms," *Nature*, Jun. 24, 1999, 399(6738 Suppl.):A7-A14.

Lee et al., "Evolution of lipid structures during model membrane fusion and the relation of this process to cell membrane fusion," *Biochemistry*, May 27, 1997; 36(21):6251-6259.

Lee et al., "Transient and stable ionic permeabilization of isolated skeletal muscle cells after electrical shock," *J. Burn Care & Rehab.*, 1993; 14(5):528-540.

Lentz, "Polymer-Induced membrane fusion: Potential mechanism and relation to cell fusion events," *Chem. Phys. Lipids*, 1994; 73:91-106.

Leskovar et al., "Giant Multinucleated Macrophages Occur within the Acute Spinal Cord Injury," *Cell & Tissue Research*, May 2001; 304(2):311-315.

Leskovar et al., "The Macrophage in Neural Injury: Changes in Cell Numbers Over Time and Levels of Cytokine Production in Mammalian Central and Peripheral Nervous Systems," *J. Exp. Biol.*, Jun. 2000; 203(12):1783-1795.

Lucas et al., "Neuronal survival or death after dendrite transection close to the perikaryon: correlation with electrophysiologic, morphologic, and ultrastructural changes," *CNS Trauma*, 1985; 2(4):231-255.

Lucas et al., "Physical injury of neurons: Important roles for sodium and Chloride ions," *The Neuroscientist*, 1997; 3(2):89-111.

Malmgren et al., "A sensitive histochemical method for light- and electron-microscopic demonstration of horseradish peroxidase," *J. Histochem. Cytochem.*, Nov. 1977; 25(11):1280-1283.

Marks et al., "Amphiphilic, tri-block copolymers provide potent membrane-targeted neuroprotection," *FASEB J*, Apr. 2001; 10:1107-1110.

Massenburg et al., "Poly(ethylene glycol)-induced and rupture of diapalmitoylphosphatidylcholine large, unilamellar extruded vesicles," *Biochem.*, Apr. 1993; 32(6):9172-9180.

Maxwell et al., "Cytochemical evidence for redistribution of membrane pump calcium-ATPase and ecto-Ca-ATPase activity, and calcium influx in myelinated nerve fibers of the optic nerve after stretch injury," *J. Neurocytology*, Dec. 1995; 24(12):925-942.

Maxwell et al., "Freeze-fracture and cytochemical evidence for structural and functional alteration in the axolemma and myelin sheath of adult guinea pig optic nerve fibers after stretch injury," *J. Neurotrauma*, 1999; 16(4):273-284.

Maxwell, "Histopathological changes at central nodes of ranvier after stretch-injury," *Microscopy Research and Technique*, May 1, 1996; 34(1):522-535.

Maxwell et al., "Loss of axonal microtubules and neurofilaments after stretch-injury to guinea pig optic nerve fibers," *J. Neurotrauma*, 1997; 14(9):603-614.

Maxwell et al., "Ultrastructural evidence of axonal shearing as a result of lateral acceleration of the head in non-human primates," *Acta Neuropathol.*, 1993; 86(1):136-144.

Mayer et al., "Effects of poloxamer 188 in a rabbit model of hemorrhagic shock," *Annals of Clinical & Laboratory Science*, 1994; 24(4):302-11.

Merchant et al., "Poloxamer 188 enhances functional recovery of lethally heat-shocked fibroblasts," *J. Surg. Res.*, Feb. 1, 1998; 74(2):131-140.

Mezrow et al., "Poloxamer 188 improves neurologic outcome after hypothermic circulatory arrest," *Journal of Thoracic & Cardiovascular Surgery*, Jun. 1992; 103(6):1143-6.

Monyer et al., "21-Aminosteroids attenuate excitotoxic neuronal injury in cortical cell cultures," *Neuron*, Aug. 1990; 5:121-126.

Mori et al., "Basic Neurophysiology of Primate Locomotion," *Folia Primatologica*, 1996; 66:192-203.

Moriarty et al., "The Effect of an Applied Electric Field on Macrophage Accumulation within the subacute spinal injury," *J. Rest. Neurolog. Neurosci.*, 1999; 14(1):53-64.

Moriarty et al., "Two and Three Dimensional Computer Graphic Evaluation of the Subacute Spinal Cord Injury," *J. of Neurological Sciences*, 1998; 155:121-137.

Naito et al., "Analyses of treadmill locomotion in adult spinal dogs," *Neurosci. Res.*, Aug. 1990; 8(4):281-290.

Nakajima et al., "Fusogenic activity of various water-soluble polymers," *J. Biomaterials Sci., Polymer Ed.*, 1994; 6(8):751-9.

Novelli et al., "Glutamate becomes neurotoxic via the N-methyl-D-aspartate receptor when intracellular energy levels are reduced," *Brain Res.*, Jun. 7, 1988; 451(1/2):205-212.

Ochs, "Chapter 1: A brief history of nerve repair and regeneration," *Nerve Repair and Regeneration: Its Clinical and Experimental Basis*, Jewett et al., eds., The C.V. Mosny Co., St. Louis, MO, 1980; 1-8.

O'Lague et al., "Physiological and morphological studies of rat pheochromocytoma cells (PC12) chemically fused and grown in culture," *Proc. Nat. Acad. Sci. USA*, Mar. 1980; 77(3):1701-1705.

O'Keefe et al., "Poloxamer-188 as an adjunct to primary percutaneous transluminal coronary angioplasty for acute myocardinal infarction," *American Journal of Cardiology*, Oct. 1, 1996; 78:747-50.

Padanlam et al., "Effectiveness of Poloxamer 188 in arresting calcein leakage from thermally damaged isolated skeletal muscle cells," *Ann. N.Y. Acad. Sci.*, May 31, 1994; 720:111-123.

Palmer et al., "Surfactant administration reduces testicular ischemia-reperfusion injury," *J. Urol.*, Jun. 1988; 159:2136-2139.

Pontecorvo, "Production of mammalian somatic cell hybrids by means of polyethylene glycol treatment," *Somatic Cell Genetics*, 1975; 1(4):397-400.

"Radiculopathies," [online]. Global Anatomy: Department of Anatomy, University of Wisconsin Medical School, 2002 [retrieved on May 16, 2002]. Retrieved from the Internet: <URL:http://www.anatomy.wisc.edu/SClinic/Radiculo/Radiculopathy.htm>. (8 pgs.).

Rivlin et al., "Effect of Duration of Acute Spinal Cord Compression in a New Acute Cord Injury Model in the Rat," *Surg. Neurol.*, Jul. 1978; 10(1):39-43.

Rivlin et al., "Objective clinical assessment of motor function after experimental spinal cord injury in the rat," *J. Neurosurg.*, Oct. 1977; 47(4):577-581.

Rosenberg et al., "Reduction of NaCl increases survival of mammalian spinal neurons subjected to dendrite transaction injury," *Brain Res.*, 1996; 734:349-353.

Rossignol et al., "Spinal pattern generation," *Curr. Opin. Neurobiol.*, Dec. 1994; 4(6):894-902.

Salzman et al., "Anesthesia influences the outcome from experimental spinal cord injury," *Brain Res.*, 1990; 521:33-39.

Schoch, "Researcher fuses spinal cords," *The Indianapolis Star*, Nov. 11, 1998; pp. 1 and 6.

Selzer, "Mechanisms of functional recovery and regeneration after spinal cord transection in larval sea lamprey," *J. Physiol.*, 1978; 277:395-408.

Sharma et al., "Poloxamer 188 decreases susceptibility of artificial lipid membranes to electroporation," *Biophys. J.*, Dec. 1996; 71:3229-3241.

Shi et al., "Anatomical repair of nerve membranes in crushed mammalian spinal cord with polyethylene glycol," *J. Neurocytol.*, 2000; 29:633-643.

Shi et al., "Compression injury of mammalian spinal cord in vitro and the dynamics of action potential conduction failure," *J. Neurophysiol.*, Sep. 1996; 76(3):1572-9.

Shi et al., "Control of membrane sealing in injured mammalian spinal cords axons," *J. Neurophysiol.*, Oct. 8, 2000; 84(4):1763-9.

Shi et al., "Sucrose-gap recording from isolated spinal cord to examine axonal pathophysiology in response to compression injury," *J. Neurotrauma*, 1995; 12:996.

Shi et al., "m-Calpain dependence of membrane sealing in mammalian spinal cord axons," *Society for Neuroscience Abstracts*, 1997; 23(1):270.

Siesjö et al., "Neurocytotoxicity: pharmacological implications," *Fundam. Clin. Pharmacol.*, 1991; 5(9):755-767.

Somerson et al., "Functional Analysis of an Electromechanical Spinal Cord Injury Device," *Exp. Neurol.*, 1987; 96:82-96.

"Spinal cord and meninges," [online]. Wheeless' Textbook of Orthopaedics. [retrieved on Feb. 20, 2002]. Retrieved from the Internet: <URL:http://www.medmedia.com/011/44.htm>. (2 pgs.).

"Spinal cord and nerve roots," [online]. Spine-health.com, 2002. [retrieved on Feb. 20, 2002]. Retrieved from the Internet: <URL:http://www.spine-health.com/topics/anat/a04.html>. (2 pgs.).

Strautman et al., "Intracellular Free calcium concentrations and gradients in severed and intact spinal axons," *J. Gen. Physiol.*, Dec. 1986; 88(6):57a-58a.

Stys et al., "Role of extracellular calcium in anoxic injury of mammalian central white matter," *Proc. Natl. Acad. Sci. USA*, Jun. 1990; 87:4212-4216.

Tator et al., "Review of the secondary injury theory of acute spinal cord trauma with emphasis on vascular mechanisms," *J. Neurosurgery*, Jul. 1991; 75(1):15-26.

Theriault et al., "Intrinsic organization of the rat cutaneus trunci motor nucleus," *J. Neurophysiol.*, Aug. 1988; 60(2):463-77.

Theriault et al., "Nociceptive cutaneous stimuli evoke localized contractions in a skeletal muscle," *J. Neurophys.*, Aug. 1988; 60(2):446-462.

Thomas et al., "Clinical aspects of PNS regeneration," *Advances in Neurology, vol. 47: Functional Recovery in Neurological Disease*, Waxman, ed., Raven Press, New York, 1988; 9-29.

Tilcock et al., "The Interaction of Phospholipid Membranes with Poly(Ethylene Glycol) Vesicle Aggregation and Lipid Exchange," *Biochem.*, 1982; 688:645-652.

Uhler et al., "The effects of megadose methylprednisolone and U-78517F on toxicity mediated by glutamate receptors in the rat neostriatum," *Neurosurgery*, Jan. 1994; 34(1):122-7; discussion 127-8.

Valentini et al., "Chapter 42: Strategies for the engineering of peripheral nervous tissue regeneration," *Principles of Tissue Engineering*, Lanza et al., eds., R.G. Landes Co., 671-684, 2003.

Wagih et al., "Validation of the American Spinal Injury Association (ASIA) Motor Score and the National Acute Spinal Cord Injury Study (NASCIS) Motor Score," *Spine*, 1991; 21(5):614-619.

Wiswedel et al., "Injury of mitochondrial respiration and membrane potential during iron/ascorbate-induced peroxidation," *Biochim. Biophys. Acta.*, Jun. 15, 1988; 934(1):80-86.

Xie et al., "Membrane resealing in cultured rat septal neurons after neurite transection: evidence for enhancement by $Ca^{2+}$-triggered protease activity and cytoskeletal disassembly," *J. Neurosci.*, 1991; 11(10):3257-3267.

Xue et al., "Intracerebral injection of autologous whole blood in rats: time course of inflammation and cell death," *Neuroscience Letters*, Oct. 2000; 283:230-232.

Yawo et al., "Calcium dependence of membrane sealing at the cut end of the cockroach giant axon," *J. Neurosci.*, Jun. 1985; 5(6):1626-1632.

Young, "Secondary injury mechanisms in acute spinal cord injury," *J. Emerg. Med.*, 1993; 11:13-22.

\* cited by examiner

A

Pre injury 60 min. post-injury

B   Control

C   PEG-treated
(Hypothetical)

D   PEG-treated

METHODS AND COMPOSITIONS FOR TREATING MAMMALIAN SPINAL CORD INJURIES

CROSS-REFERENCE TO RELATED APPLICATIONS

The present application claims the benefit of U.S. Provisional Application Ser. No. 60/108,145, filed on Nov. 12, 1998, which is hereby incorporated by reference in its entirety.

This invention was made with government support under grant number DAMD17-94-J-4242 awarded by the Department of the Army and grant number BES9631560 awarded by the National Science Foundation. The Government has certain rights in the invention.

BACKGROUND OF THE INVENTION

The present invention relates generally to methods for treating an injured spinal cord. Specifically, the invention relates to methods for treating an injured spinal cord that include contacting the spinal cord with a biomembrane fusion agent. Pharmaceutical compositions for treating an injured spinal cord are also described.

The devastating effects of injury to the mammalian spinal cord are not immediate. Severe mechanical injury initiates a delayed destruction of spinal cord tissue producing a loss in nerve impulse conduction associated with a progressive local dissolution of nerve fibers (axons) [Honmou, O. and Young, W. (1995) *The Axon* (Waxman, S. G., et al., Eds.) pp. 480-529, Oxford University Press, New York; Griffin, J. W. et al. (1995) *The Axon* (Waxman, S. G., et al., Eds.) pp. 375-390, Oxford University Press, New York]. This loss of sensory and motor communication across the injury site can produce a permanent paralysis and loss of sensation in regions below the level of the spinal injury. Furthermore, it is clear the most damaging effects of progressive "secondary injury" [Young, W. (1993) *J. Emerg. Med.* 11:13-22] of spinal cord parenchyma relative to the loss of behavioral functioning is the effect it has on white matter. Localized mechanical, biochemical, and anoxic/ischemic injury to white matter may be sufficient to cause the failure of axolemmas to function as a barrier or fence to the unregulated exchange of ions [Honmou, O. and Young, W. (1995) *The Axon* (Waxman, S. G., et al., Eds.) pp. 480-529, Oxford University Press, New York]. This in turn compromises both the structural integrity of this region of the nerve fiber and its ability to conduct impulses along the cable. For example, elevated intracellular $Ca^{2+}$ induces depolymerization of microtubules and microfilaments producing a focal destruction of the cytoskeleton Griffin, J. W. et al. (1995) *The Axon* (Waxman, S. G., et al., Eds.) pp. 375-390, Oxford University Press, New York]; Maxwell, W. L., et al. (1995) *J. Neurocytology* 24:925-942]; Maxwell, W. L., et al. *J. Neurotrauma* 16:273-284]. When $K^+$ rushes down its electrochemical gradient out of the cell, the resultant elevated extracellular concentration contributes to localized conduction block [Honmou, O. and Young, W. (1995) *The Axon* (Waxman, S. G., et al., Eds.) pp. 480-529, Oxford University Press, New York; Shi, R. et al., (1997) *Society for Neuroscience Abstracts*, 108:16].

Methods and compositions for treating mammalian spinal cord injuries are needed. The present invention addresses these needs.

SUMMARY OF THE INVENTION

It has been discovered that contacting an injured spinal cord of a vertebrate with a biomembrane fusion agent treats cellular damage such that function is at least partially restored. Accordingly, one aspect of the invention provides a method of treating an injured mammalian, preferably human, spinal cord that includes contacting the cord with an effective amount of a biomembrane fusion agent. In one form of the invention, the biomembrane fusion agent is a polyalkylene glycol, such as polyethylene glycol. In one form of the invention, a method of treating an injured mammalian spinal cord also includes contacting the spinal cord with an effective amount of a potassium channel blocker. The potassium channel blocker can be, for example, an amino-substituted pyridine, such as 4-aminopyridine. The biomembrane fusion agent is preferably a polyalkylene glycol, such as polyethylene glycol.

Yet other aspects of the invention provide compositions for treating an injured mammalian nervous system, such as an injured mammalian spinal cord, that include effective amounts of a biomembrane fusion agent and a potassium channel blocker as described above. It has been unexpectedly found that such compositions synergistically treat a damaged spinal cord.

It is therefore an object of the invention to provide methods and compositions for treating a mammalian spinal cord to at least partially restore nerve function.

These and other objects and advantages of the present invention will be apparent from the descriptions herein.

BRIEF DESCRIPTION OF THE FIGURES

FIG. 1A depicts a top view of the double sucrose recording chamber. In FIG. 1A, from left to right, the first large compartment contains 120 mM KCl, the central large compartment contains the physiological test solutions, such as oxygenated Krebs' solution, and the third compartment also contains 120 mM KCl. The small chambers on either side of the central compartment contain 230 mM sucrose. Seals fashioned from coverslips are secured in place with high vacuum silicone grease at the locations shown to inhibit the exchange of the various media from one compartment to the next. AgAgCl electrodes for recording and stimulation are in series with socket connectors at the locations shown. In the top portion of FIG. 1B, a side view of the apparatus used to produce a standardized crush to the isolated spinal cord at its midpoint within the central compartment is shown. The position of the spinal cord injury within the central chamber is shown in the lower portion of FIG. 1B. The apparatuses are further described in example 1.

FIG. 4A depicts a series of 10 superimposed electrophysiological recordings showing CAPs in response to 10 separate increasing stimulus intensities (0.015-2.0 mA, 100 µs duration squarewave stimuli) prior to the experimental crush and 1 hour after the crush in a control preparation. FIG. 4B is graph showing the preinjury amplitude vs. post injury amplitudes for 4 spinal cord strips in a modestly injured control group. FIG. 4C shows a graph of preinjury amplitude vs. post-injury amplitudes showing the hypothetical skewing of data where (a) more large caliber fibers (with a lower stimulus threshold) are responsible for the CAP or (c) more small caliber fibers are recruited to produce the recovered CAP following injury relative to unity (b). FIG. 4D shows the actual distribution of these data points in the PEG-treated group.

In FIG. 5A, twenty individual records of CAP responses to twin pulse stimuli are superimposed. The first of these twenty stimuli produced the single large CAP marked with the arrow. Since this first CAP is always produced by a stimulus of the same intensity, each of these superimposed individual electrical records was identical. From left to right, the CAP produced by the second stimulus is shown. Note the typical dampened amplitude of the second CAP when triggered during the relative refractory period followed by the typical plateau in amplitude produced when the second stimulus is applied subsequent to the relative refractory period. In FIGS. 5B and 5C, the response to the secondary stimulus (as a % of the first CAP amplitude) vs. the interstimulus interval is plotted for 4 untreated and PEG-treated spinal cord strips, respectively. Filled circles show data points prior to the standardized crush injury while open circles show data points obtained 1 hour after the injury.

In FIG. 6A, untreated spinal cord strips were treated with 100 μM 4-AP at 1 hour post-injury. FIG. In FIG. 6B, 100 μM 4-AP was administered 1 hour post-PEG application.

FIG. 9A shows a normal compound action potential (CAP) recorded from a strip of ventral white matter prior to cutting the spinal cord. Two minutes after this record was taken, the strip was completely severed transversely, eliminating CAP conduction to the recording site as seen in FIG. 9B. Although the CAP began to recover within 15 minutes of PEG application, FIG. 9C shows the weak recovering compound action potential 60 minutes post transection. FIG. 9D is typical of all fused cords tested, where a second transection through the fusion plane eliminated the recovered CAP. FIGS. 9 E-H show the results of control experiments. FIG. 9E shows a typical CAP. In FIG. 9F, this CAP was subsequently eliminated following transection when the two segments of white matter were tightly abutted and treated identically to the fusion procedures except that PEG was not applied. In FIG. 9G, another typical CAP is shown. After transection, the spinal cord strips used to obtain FIG. 9G data were loosely abutted following complete transection and PEG was applied. Note the lack of any recovered CAP in FIG. 9H. FIG. 1 shows another recovered CAP produced by PEG fusion at the same level of amplification as shown in FIG. 9C. All traces represent a computer average of 20 individual records. The scale bar in FIG. 9A is for FIGS. 9A, 9B, and 9D. The scale bar in FIG. 9E is for FIGS. 9E-H.

In FIG. 11C, the arrows point to three of many terminal clubs of unfused fibers within the FE injected segment of the cord mingling with fused fibers traced across the original plane of transection. The arrows in FIG. 11D point to two FR-labeled fused axons that could be traced across to the opposite cord segment. The asterisk (*) marks one nearby unfused axon ending in a terminal club near the transection plane. In FIG. 11E, a 1 micron plastic embedded section is shown, displaying a region of axon reattachment. FIG. 11F is a higher magnification view of a plastic section adjacent to one shown in FIG. 11E, and shows that the site of continuity is produced by a collection of abnormal, unmyelinated axon segments which are in continuity with myelinated axons in both halves of the white matter strip. The scale bars are: FIG. 11A=50 μm, FIG. 11C=25 μm, FIG. 11D=20 μm, FIG. 11E 10 μm, and FIG. 11F=5 μm.

FIG. 12C shows the receptive field prior to spinal cord injury (green). The region circumscribed in red is a superimposed image 4 days post injury which shows the region of CTM loss. Within this region, tactile stimulation no longer produced contraction of the skin. In this sham-treated animal, CTM functioning remained unchanged until sacrifice 1 month post-injury. FIG. 12D shows behavioral recovery following PEG application: From left to right, the first drawing shows the normal CTM receptive field prior to spinal cord injury. The second drawing shows the undamaged receptive field (green) and the region of CTM loss (red) is shown prior to the application of PEG. The third drawing shows the same guinea pig 4 days following the application of PEG. The region of CTM behavioral recovery, which was observed within the first 6 hours post PEG application and which increased in size with time to restore about 29% of the area of CTM behavioral loss by 4 days post injury, is outlined in blue.

In FIG. 13C, SSEPs are shown before and after PEG application. From top to bottom: a typical SSEP prior to spinal cord injury; an SSEP showing immediate loss of the SSEP following injury; SSEP of a median nerve control; SSEP 1 hour post PEG; SSEP 1 day post PEG; and SSEP 4 days post-PEG. FIG. 13D depicts a graph of the mean and standard error of both amplitude and latency of the early arriving (PI) SSEPs in 10 PEG-treated animals as a function of time after crush.

FIG. 14A shows a typical SSEP prior to compression of the spinal cord and its elimination following injury as in FIGS. 13B-13D. FIG. 14B depicts SSEP electrical recordings of control, sham-treated animals, after various indicated time periods. SA=stimulus artifact; P1=first arriving SSEP (latency=about 18 ms); P 2=late arriving potentials (latency=about 34 ms). FIG. 14C depicts an electrical recording showing SSEPs after delayed treatment with PEG.

DESCRIPTION OF THE PREFERRED EMBODIMENTS

Figure 1A:
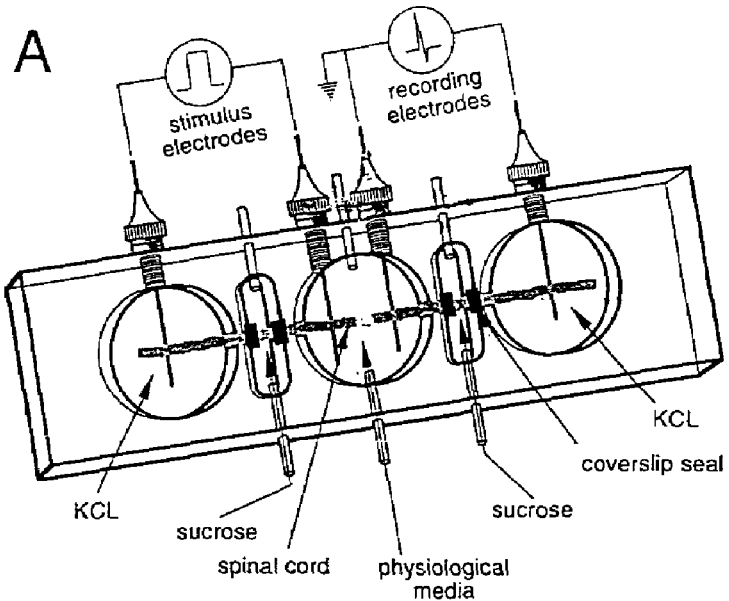
FIGS. 1A-1B depict experimental apparatuses used in the study.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides methods and compositions for treating an injured spinal cord of a vertebrate. The methods are designed to at least partially restore nerve function in the vertebrate. In one aspect of the invention, methods are provided for treating an injured or damaged vertebrate spinal cord that include contacting the spinal cord with an effective amount of a biomembrane fusion agent. The biomembrane fusion agent is preferably a polyalkylene glycol, such as polyethylene glycol. In alternative embodiments, the method may include treating the nervous system with a potassium channel blocker, preferably a substituted pyridine, such as an amino-substituted pyridine, either before, during or after contacting the spinal cord with the biomembrane fusion agent. Other aspects of the invention provide compositions for treating an injured nervous system of a vertebrate. The preferred compositions include a biomembrane fusion agent and a potassium channel blocker.

As indicated above, in a first aspect of the invention, a method of treating an injured spinal cord of a vertebrate is provided. The method is preferably performed in vivo, although it may also be used in vitro, for example, in the study of spinal cord components or functionality.

The preferred biomembrane fusion agent is a polyalkylene glycol. A wide variety of polyalkylene glycols may be used, including those, for example, where the alkylene group is methylene, ethylene, propylene, butylene, pentylene, hexylene, heptylene, octylene, nonylene, and decylene, including branched and structural isomers thereof. Preferably, the polyalkylene glycol will be water-soluble. A more preferred polyalkylene glycol is polyethylene glycol. Although a wide range of molecular weight polyalkylene glycols may be used, polyalkylene glycols of molecular weight of about 400 to about 3500 daltons are preferred. Such biomembrane fusion agents may be synthesized by methods known to the art or may be purchased commercially.

The biomembrane fusion agent may also be a polyalkylene glycol/protein conjugate as known in the art, wherein the protein preferably aids in scavenging free radicals. For example, the biomembrane fusion agent, such as polyethylene glycol, may be conjugated to catalase to form PEG-catalase, or to superoxide dismutase to form PEG-SOD. Such conjugates are available commercially from Sigma®, St. Louis, Mo.

The biomembrane fusion agent may be provided in a pharmaceutically acceptable carrier. Such carriers include, for example, water, preferably sterile and including distilled water, and any other pharmaceutically acceptable carrier known to the art that will not have an adverse effect on the treatment. Sterile distilled water is a preferred carrier in work to date. Although the percentage by weight of the fusion agent in the composition may vary, the composition typically includes at least about 40% of the fusion agent by weight, more preferably about 40% to about 50% by weight, and most preferably about 50% to about 55% by weight.

The biomembrane fusion agent is desirably applied to the site of injury as soon after injury as possible and prior to unreversible dissolution of axonal membranes and the myelin sheath. Although this time period may vary depending on the nature and extent of the injury, the fusion agent is typically applied immediately after the injury occurs, and preferably not later than about 24 hours post-injury, but is typically applied between about 1 hour to about 5 hours post-injury.

The biomembrane fusion agent may be administered to the site of injury by any suitable method. For example, the agent may be applied to a surgically exposed injury with any suitable liquid dispensing device. The injured site is exposed to the fusion agent for a time period effective for treating the injury. This time may vary depending on the size of the lesion, the extent and nature of the injury, the biomembrane fusion agent used, and the concentration of the biomembrane fusion agent. The lesion is typically exposed to the agent for at least about one minute and more preferably at least about 2 minutes. In preferred embodiments, the fusion agent is removed from the injured tissue being treated prior to the occurrence of deleterious tissue changes. In a further preferred embodiment, the injured tissue is exposed to the fusion agent for no more than about 5 minutes. After the injured region of the nervous system is treated with the fusion agent, it may be removed by aspiration and the treated site washed with a biowashing solution, such as isotonic Kreb's solution as described in the examples. Excess fusion agent and/or Kreb's solution can then be removed by aspiration.

In another form of the invention, the method may include contacting the injured site with an effective amount of a potassium channel blocker in addition to a biomembrane fusion agent. A variety of potassium channel blockers may be used, including substituted pyridines. Preferred potassium channel blockers include those that improve action potential conduction in injured tissue, including 3,4-diaminopyridine, 4-methylaminopyridine and ampidine. In a preferred form of the invention, the pyridine is substituted with an amino group, more preferably at the 4-position of the ring. Moreover, it has unexpectedly been discovered that treatment of an injured mammalian spinal cord with a potassium channel blocker, such as 4-aminopyridine, after treatment with a fusion agent, such as polyethylene glycol, can result in synergistic repair of the spinal cord. For example, CAPs increase in conduction when both agents are used by a percentage greater than the sum of the percent increase in conduction of the CAPs when injured spinal cords are treated alone with either the fusion agent or the potassium channel blocker.

Although the injured nervous system may be contacted with the potassium channel blocker prior to or at the same time as treating with the fusion agent, the system is preferably contacted with the blocker after the treatment with the fusion agent. The potassium channel blocker may be applied in a fashion similar to the fusion agent. The amount of the potassium channel blocker effective in treating or repairing the injured nervous system, such as injured mammalian spinal cord, will also similarly depend on the factors mentioned above. When the potassium channel blocker is 4-aminopyridine, it is typically applied at a concentration of about 10-100 ng/ml cerebrospinal fluid and further preferably about 50-100 ng/ml cerebrospinal fluid. After treatment with 4-aminopyridine, it can similarly be removed by aspiration and the lesion site washed with the biowashing agent.

In yet other forms of the invention, the method may include treating the injury with a polyalkylene glycol, as well as with other conventional management compounds and/or compositions. For example, in addition to treatment with a polyalkylene glycol, the injury may be treated with a steroid, such as methylprednisolone.

A wide variety of injuries may be treated in the present invention. In various forms of the invention, the injury may arise from a compression or other contusion of the spinal cord, crushing of the spinal cord or severing of the spinal cord.

The efficacy of the treatment may be determined in a variety of ways, including methods which detect restoration of nerve function. For example, restoration or increase in conduction of action potentials, such as CAPs, through the injured site may be used as an indicator that nerve function has at least partially been restored as described in the examples. Nerve function is considered to have been at least partially restored if there is an increase in the conduction of action potentials after treatment. Preferably, the treatment will be conducted sufficiently to achieve at least about 10% increase in conduction of CAPs. Moreover, restoration of anatomical continuity may also be observed by examination with high-resolution light microscopy and/or by diffusion of intracellular fluorescent dyes through the repaired nervous tissue, such as repaired axons, or by direct observation of repaired axonal membranes. Additionally, in human applications, the efficacy of preferred treatments may be observed by the restoration of more than one spinal root level as determined by the American Spinal Injury Association (ASIA) motor score and/or the National Animal Spinal Cord Injury Study (NASCIS) score as know in the art and as described in Wagih et al., (1996) *Spine* 21:614-619. Furthermore, in veterinary applications, behavioral analysis of the cutaneous trunci muscle (CTM) reflex, as more fully discussed in the examples, may also be used to determine the efficacy of the treatment, and whether nerve function has at least partially been restored. Using this analysis, nerve function is considered to have been at least partially restored if there is an increased reflex behavior after treatment, but treatments are desirably preferred so as to achieve at least about a 10% increase in the area of CTM behavioral recovery.

In yet other aspects of the invention, compositions for treating an injured nervous system of a vertebrate are provided. The compositions are designed to at least partially restore nerve function as described below. In one form of the invention, a composition includes effective amounts of a biomembrane fusion agent and a potassium channel blocker. Although a wide variety of biomembrane fusion agents and potassium channel blockers that are mentioned above may be included in the composition, a preferred biomembrane fusion agent is a polyalkylene glycol and a preferred potassium channel blocker is a substituted pyridine. In more preferred forms of the invention, the polyalkylene glycol is polyethylene glycol and the potassium channel blocker is an amino-substituted pyridine, such as 4-aminopyridine. The composition may be in a pharmaceutically acceptable carrier as described above.

Although the methods and compositions of the invention are useful in treating a wide variety of vertebrates, they may be advantageously used to treat mammals and preferably humans. Moreover, although the methods and compositions are advantageously and surprisingly useful in treating the spinal cord, they may also be used in treating the peripheral nervous system and/or central nervous system, or other areas in which damaged axons are present.

Reference will now be made to specific examples illustrating the compositions and methods described above. It is to be understood that the examples are provided to illustrate preferred embodiments and that no limitation to the scope of the invention is intended thereby.

EXAMPLE 1

Acute In Vitro Response of Crushed Spinal Cord to PEG

This example demonstrates that compound action potentials are restored in a compressed spinal cord in vitro after it is treated with PEG.

In Vitro Isolation of the Spinal Cord

Adult female guinea pigs of 350-500 gram body weight were used for these studies. The spinal cord was isolated from deeply anesthetized animals [(60 mg/kg ketamine hydrochloride, 0.6 mg/kg acepromazine maleate, and 10 mg/kg xylazine, intramuscularly (i.m.)]. Following anesthesia, the animal was perfused transcardially with cold (15° C.) Krebs' solution (NaCl, 124 mM; KCl, 2 mM; $KH_2PO_4$, 1.2 mM; $MgSO_4$, 1.3 mM; $CaCl_2$, 1.2 mM; dextrose, 10 mM; $NaHCO_3$, 26 mM; sodium ascorbate, 10 mM; equilibrated with 95% $O_2$, and 5% $CO_2$). The vertebral column was rapidly removed using bone forceps and scissors by previously described techniques [Shi, R. and Blight, A. R. (1996) *J. of Neurophysiology*, 76(3):1572-1579; Shi, R. and Blight, A. R. (1997) *Neuroscience* 77(2):553-562]. The spinal cord was divided into four longitudinal strips, first by midline sagittal division, then by separating the dorsal and ventral halves with a scalpel blade against a plastic block. Only the ventral white matter was used for this study. These 35-38 mm long strips of spinal cord white matter will usually be referred to below as "cords" or "spinal cords" for ease of description. Spinal cords were maintained in continuously oxygenated Krebs' solution for an hour before mounting them within the recording chamber. This was to ensure their recovery from dissection before experiments were begun.

Double Sucrose Gap Recording Technique

Figure 1B:
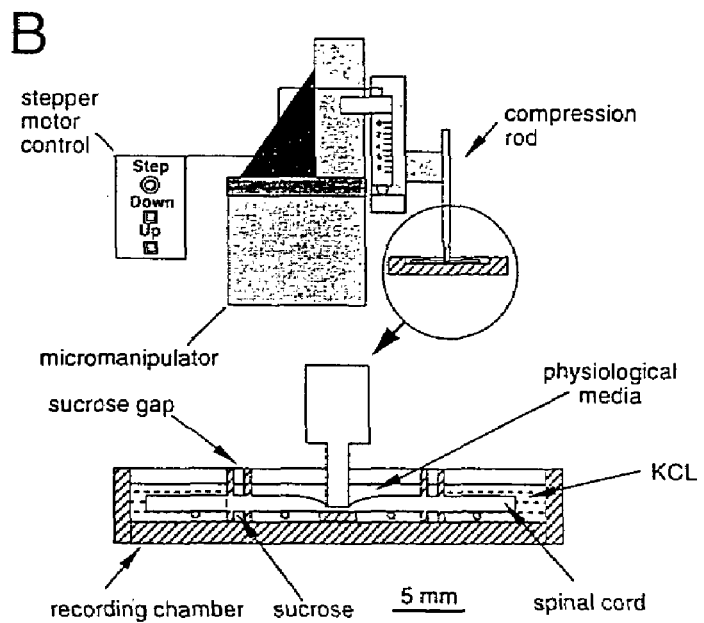

The double sucrose gap recording chamber is shown in FIGS. 1A and 1B and has already been described in previous publications [Shi, R. and Blight, A. R. (1996) *J. of Neurophysiology*, 76(3):1572-1579; Shi, R. and Blight, A. R. (1997) *Neuroscience* 77(2):553-562]. Briefly, the strip of isolated spinal cord white matter was supported in the three-compartment chamber. The central compartment was continuously superfused with oxygenated Krebs' solution (about 2 ml/min) with a peristaltic pump. The compartments at both ends were filled with isotonic (120 mM) potassium chloride, and the gap channels with 230 mM sucrose. The white matter strip was sealed on either side of the sucrose gap channels with shaped fragments of glass coverslips that also blocked the flow of fluid in the narrow gap between the coverslip and the tissue surface. Note that the central chamber is at ground potential for recording. The sucrose solution was run continuously through the gap at a rate of 1 ml/min. Axons within the spinal cord strip were stimulated and compound action potentials (CAPs) were recorded at the opposite end of the white matter strip by silver-silver chloride electrodes positioned within the side chambers and the central bath as shown in FIG. 1B. Specifically, action potentials were stimulated at the left side of the spinal cord strip as shown in the figure, conducted through the spinal cord in the central compartment (also including the injury site), and recorded at the right side of the spinal cord strip as shown. Stimuli were delivered through stimulus isolation units in the form of 0.1 msec constant current unipolar pulses. A conventional bridge amplifier with capacity compensation (Neurodata Instruments) was used to amplify the signal. This data was digitized and stored on video tape with a Neurodata Instruments Neurocorder for subsequent analysis. During the experiment, the oxygenated Krebs' solution continuously perfused the isolated spinal cord tract, while temperature was maintained at 37° C.

Every electrophysiological test was digitized in real time and captured to the computer for subsequent quantitative evaluation. All records were also recorded on VHS magnetic tape as a means of back up documentation. All solutions used in the PEG repair process were made on the day of their use.

The Compression Injury

A standardized compression injury was produced with a stepper-motor controlled rod which compressed the spinal cord while suspended inside the recording chamber (FIG. 1B). Briefly, the isolated white matter strip was compressed against a flat, raised plastic, plexiglass stage at the center of the recording chamber with the flattened tip of a plexiglass rod. The tip was advanced downward to contact the tissue at a standardized rate of about 25 µm/s. The downward movement of the rod was controlled with a stepper motor to produce a finely graded crush just sufficient to eliminate all CAP propagation (which was monitored continuously during the procedure). The end of the rod with the flattened tip provided a compression surface of 2.5 mm along the length of the tissue, and a transverse width of 7 mm, such that it was always wider than the spinal cord strip, even under full compression. Positioning of the compression rod was accomplished with a micromanipulator. CAPs were simultaneously recorded during the injury process. Compression was stopped when CAPs were completely eliminated. The state of complete CAP failure was maintained for an additional 15 seconds before the rod was rapidly withdrawn from the cord's surface to relieve pressure. The recovery of the CAP was then documented. The basic recovery profile following such standardized compression in normal Krebs' solution has been previously characterized and published [Shi, R. and Blight, A. R. (1996) *J. of Neurophysiology*, 76(3):1572-1579]

PEG Repair Procedure

The PEG repair procedure included the following steps:

1) Typical physiological functioning of the isolated white matter strip removed to the recording chamber required about ½ to 1 hour of incubation time while immersed in oxygenated Krebs' to stabilize. In initial experiments, once the CAP propagation had stabilized, the Krebs' solution was replaced with $Ca^{2+}$-free Krebs' ($Ca^{2+}$ replaced with an equimolar amount of $Mg^{2+}$).

2) The spinal cord strip was then crushed by the techniques described above, while simultaneous stimulation and recording continued.

3) A solution of PEG in distilled water (50% by weight) was applied by a pressure injection through a micropipette. A vital dye was added to the PEG solution to monitor its continuous application to the lesion site in a stream about 0.5 mm wide for about 1-2 minutes. The PEG was applied to one side of the lesion, washed over it, and immediately removed by constant aspiration on the other side using a second pipette.

4.) Immediately following the PEG application, the bathing media in the central chamber was replaced with a continuous stream of oxygenated normal Krebs' solution. The physiological properties of the PEG-treated spinal cord were monitored continuously for 1 hour. Usually, a weak recovering CAP was evident within 6-15 minutes of the PEG application.

The above-described technique should be considered as a basic one, from which testing of several variations described below was performed. For example, we tested the response of "recovering" axons to the additional application of the fast potassium channel blocker, 4-aminopyridine (4-AP). In this trial, 5 separate cords were treated with an application of PEG as described above and compared to 5 control cords. One hour after compression, 100 µM 4-AP (in Krebs' solution) was applied for 15 minutes and then washed free with normal Krebs' solution as described above.

In a final series of experiments, a determination of whether it was necessary to carry out the methods of the present invention in $Ca^{2+}$-free media was made. In these experiments, the cord was compressed while it was immersed in normal Krebs' solution.

Statistical Treatment

Before and after the application of 4-AP, Student t tests were used to compare recovering action potential amplitude between the control and PEG-treated group. Comparisons of action potential amplitude were also made between the two PEG-treated groups.

Results

PEG-Mediated Repair of Crushed Spinal Cord Strips

Figure 2:
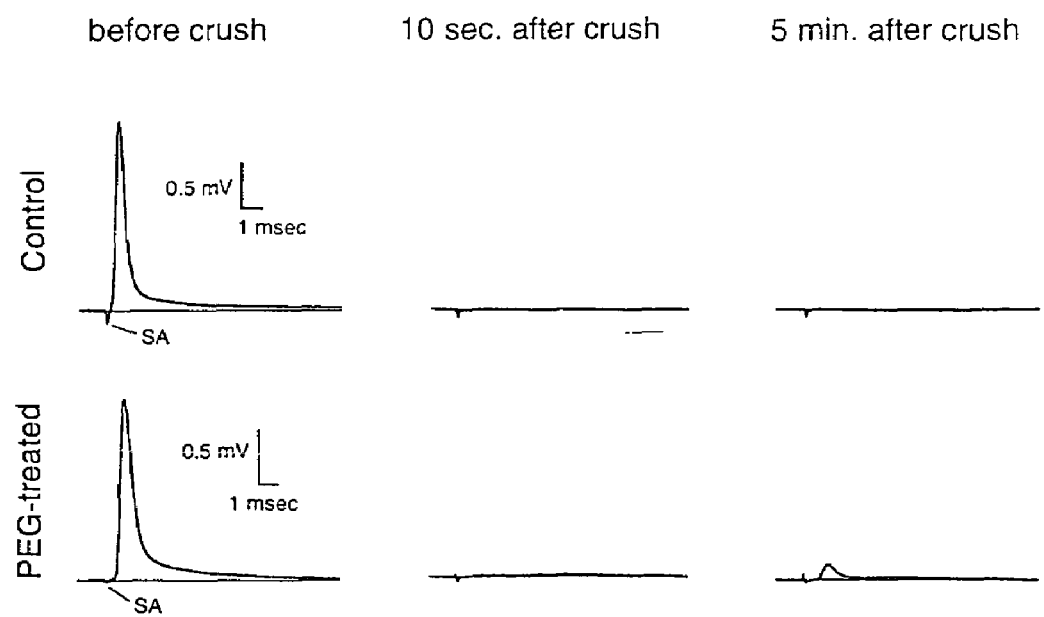
FIG. 2 depicts electrophysiological recordings of control and PEG-treated guinea pig spinal cords at 10 seconds and 5 minutes after crushing as more fully described in example 1. Top panel: electrophysiological recordings show the compound action potentials (CAPs) before the standardized experimental crush and the immediate loss of conduction after experimental injury. Bottom panel: electrophysiological recordings show a typical response to acute standardized injury of the isolated spinal cord strip after PEG treatment. SA, stimulus artifact.

Approximately ½ hour following the equilibration of the spinal cord strip in the recording chamber, the Krebs' solution in the central compartment was replaced with a $Ca^{2+}$-free Krebs' and the spinal cord was crushed by previously described techniques. In every spinal cord tested in this group of twenty (ten control and ten experimental), this procedure resulted in the immediate and total loss of CAP propagation from the point of stimulation to the point of recording. FIG. 2 shows an individual record of one typical control experiment and a PEG-treated experimental spinal cord strip. Note the immediate and complete loss of the CAP in both preparations, and the initial recovery of the CAP in the PEG-treated spinal cord by 5 minutes post treatment (FIG. 2, lower panel). Note that at the earliest time point (about 5 minutes postinjury) seen in FIG. 2, recovery of a CAP is never observed in the absence of PEG treatment and rarely occurs by 10 minutes postinjury (latter data not shown). The earliest recorded recoveries of a CAP occurred within 1-2 minutes following PEG treatment. In control preparations, 3 cords never regained conduction during the 1 hour of continuous observation. In contrast, not one PEG-treated spinal cord providing the data summarized in FIG. 3 failed to recover CAP conduction following PEG treatment. In four more control spinal cords, the recovery of the CAP was not observed for approximately twenty minutes.

Figure 3:
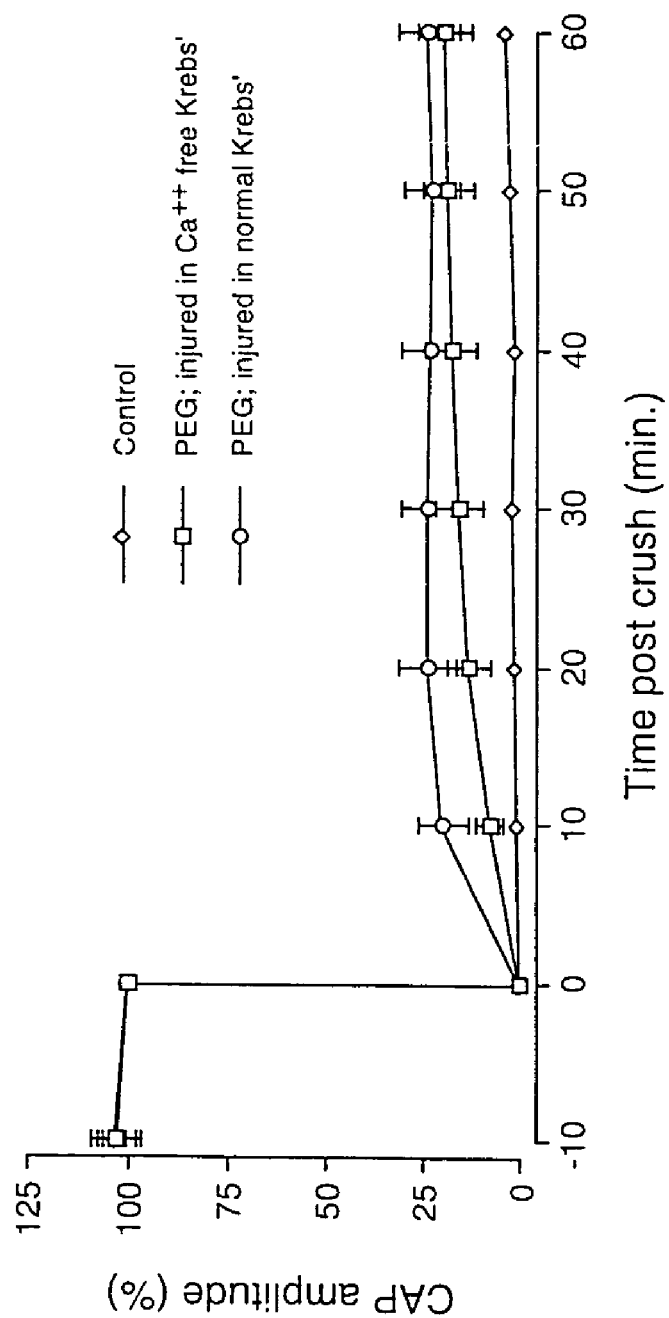
FIG. 3 depicts a graph showing the recovery of the CAP as a percentage of the precut amplitude as a function of time post-crush. Average CAPs and their standard error (SE) are displayed for 10 spinal cord strip for each group.

FIG. 3 provides a summary graph of the 10 control and the 10 experimental spinal cords treated and monitored identically, except for the experimental application of PEG to the lesion site. Note that the control group shows a barely detectable CAP (3.6%) even by 1 hour post injury, while average recovered CAPs in PEG-treated cords increase approximately 19%, ranging to as much as 69% of the pre-crush amplitude. PEG treatment always 1.) provided a striking increase in the amplitude of recorded CAPs, averaging 19% of the original pretransection amplitude and 2.) facilitated the CAP recovery in 100% of the cases tested. At every time point tested, including the 10 minute post injury period, recovered CAP amplitudes were statistically significantly greater than control preparations ($P<0.05$, Student's t test, two-tailed). CAP recovery was facilitated when the injury was not carried out in $Ca^{2+}$-free Krebs' solution. The amplitude of the recovered CAP in normal Krebs' at the first time point (10 minutes post injury) was statistically elevated over the recovered CAP observed when the injury was performed in $Ca^{2+}$-free media ($P<0.05$; unpaired student t test). Every subsequent time point was still higher in this data set with no reverse trends, but without statistical significance. Thus, it is seen in FIG. 3 that the injury need not be carried out in $Ca^{2+}$-free media to produce functional repair as claimed by Bittner for invertebrate axons [Krause, T. L. and Bittner, G. D. (1990) *PNAS* 87:1471-1475].

Electrophysiological Properties of the Repaired Spinal Cords

The PEG-repaired spinal cords showed typical conduction properties (as observed in recovering untreated cords) however some differences in their electrophysiological properties were revealed by further evaluation.

Figure 4A:
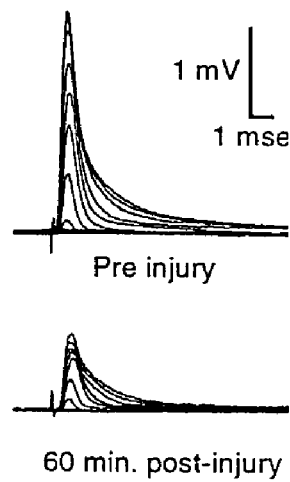
FIGS. 4A-4D depict analyses of the CAP amplitude as a function of increased strength of stimulus in control and PEG-treated spinal cords.
Figure 4B:
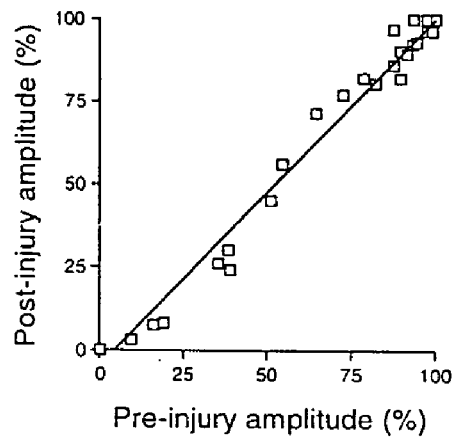

FIG. 4A shows the effect of injury on the normal recovery of CAP amplitudes. Typically, the recovered CAP was dampened in amplitude across all threshold intensities of excitation. We also evaluated if this reduced magnitude of the CAP occurred across all caliber spectra of injured axons within the spinal cord strip, or was manifest in only large or small diameter axons. FIG. 4B shows the actual amplitudes of control compound potentials at 1 hour post injury, plotted against the preinjury amplitude at the same stimulus intensity. A less severe injury was required in these spinal cords to allow an adequate range of recovered CAP amplitudes for this graded evaluation. In the severely injured cords, the maximal recovered CAPs were insufficient to adequately make these comparisons. These data points are shown relative to the maximum amplitude achieved prior to and after injury. A least squares linear regression was not significantly different from 1:1 linearity, suggesting that there was no difference between the susceptibility to damage of axons of different stimulus thresholds.

Figure 4C:
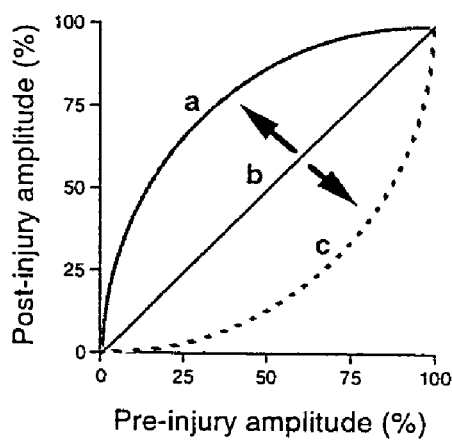
Figure 4D:
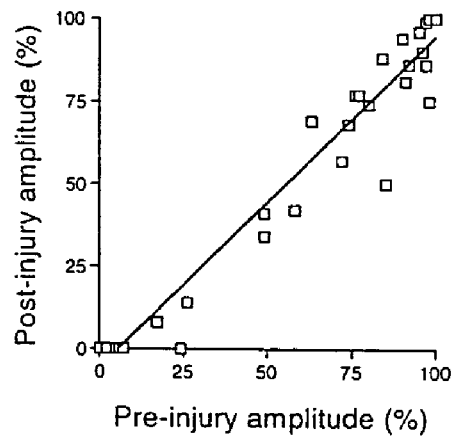

In FIG. 4C, two hypothetical lines are plotted, representing outcomes following PEG treatment. Note that if larger axons of a lowered stimulus threshold were more susceptible to PEG, the data would be shifted as in line (a). In the opposite situation, the hatched line (c) shows a shift in the opposite direction should small caliber axons with a higher stimulus threshold be repaired. In FIG. 4D, the actual data taken from the PEG-treated population is plotted in the same manner as in FIG. 4B. Note that the least square linear regression line is not significantly different from 1:1 linearity, which is again not different from that shown in FIG. 4B. The near unity slope of the relation of amplitude response before and after injury indicated no consistent selectivity of PEG-mediated improvement of conduction in fibers of lower or higher threshold. In this test, the typical and severe standardized injury was used, since PEG-repaired cords showed substantial CAPs sufficient for a graded plot of their amplitudes.

Figures 5A, 5B, 5C:
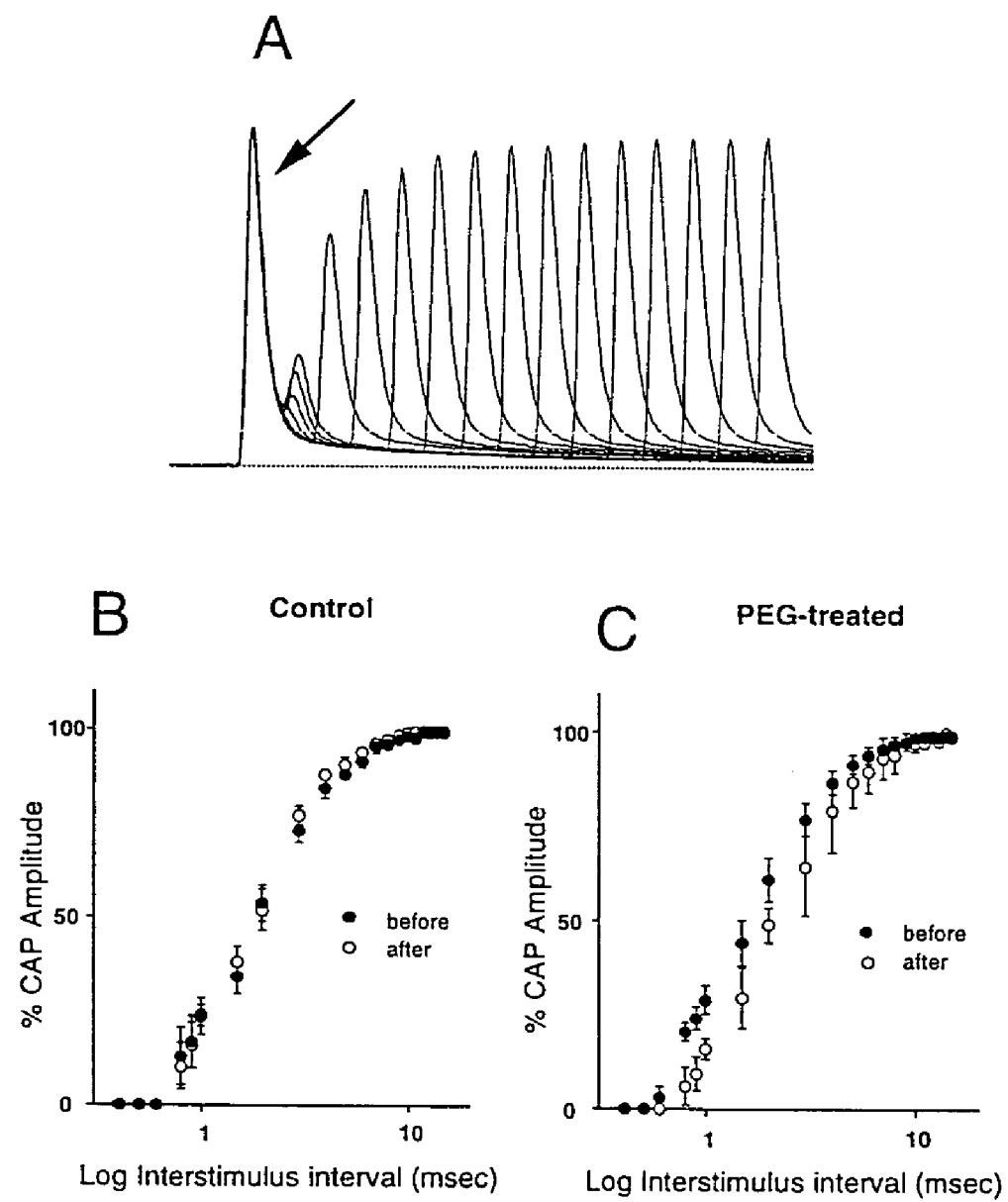
FIGS. 5A-5C depict graphical representations of refractory period changes in control and PEG-treated spinal cords after double pulse stimuli.

Although PEG appeared to be able to repair axons of a wide range of calibers similar to the natural recovery process observed in control cords, the electrophysiological properties of PEG-mediated recoveries was not the same as controls. FIG. 5A shows the classical relationship between the timing of paired stimuli and the amplitude of the two elicited CAPs. Paired stimuli in which the interstimulus interval was between 0.6 to 15.0 ms demonstrated typical dampening of the CAP amplitude soon after the absolute refractory period. When the interval between the paired stimuli was longer than this, a plateau was reached where the first and second CAPs were of an identical magnitude, marking the extent of the relative refractory period.

FIG. 5B shows control data derived from 4 separate experiments. The abscissa shows the magnitude of the second CAP of the pair as a percent of the magnitude of the first elicited CAP. The ordinate shows the log of the interstimulus interval ranging from 0.6-15 ms. This sigmoidal plot is typical, beginning with stimuli that do not elicit a second AP during the absolute refractory period, and ending at the termination of the relative refractory period.

Furthermore, FIG. 5B shows that this relationship was not disturbed by the injury, as pre- and postinjury data points were not significantly different along this sigmoidal curve. This did not hold true, however, for PEG-treated spinal cords. The early and robust recovery of CAPs produced by PEG demonstrated a typical period of absolute refractory as before the injury and experimental treatment. Furthermore, the relative refractory period also appeared to terminate when a similar stimulus interval to control preparations was achieved. During the refractory period of PEG-treated cords, the amplitude of the second CAP was slightly reduced when compared to that before the crush and PEG treatment (FIG. 5C). However, this latter relationship was not statistically significant.

EXAMPLE 2

Potassium Channel Blockade as an Adjunct to PEG-Mediated Recovery of Conduction

This example shows that treatment of injured spinal cords in vitro with both a potassium channel blocker and a biomembrane fusion agent allows synergistic recovery of CAPs.

It is a common feature of injured cells to loose intracellular potassium to the extracellular milieu through compromised membrane. In axons, this may be sufficient to suppress action potential conduction. Thus, it was attempted to determine if blockage of fast potassium channels with 4-AP would affect the properties of conduction immediately following PEG repair.

Spinal cords were crushed, isolated and treated with PEG as described in example 1. Analysis was also performed in the double sucrose recording chamber as described in example 1.

Figures 6A, 6B, 6C:
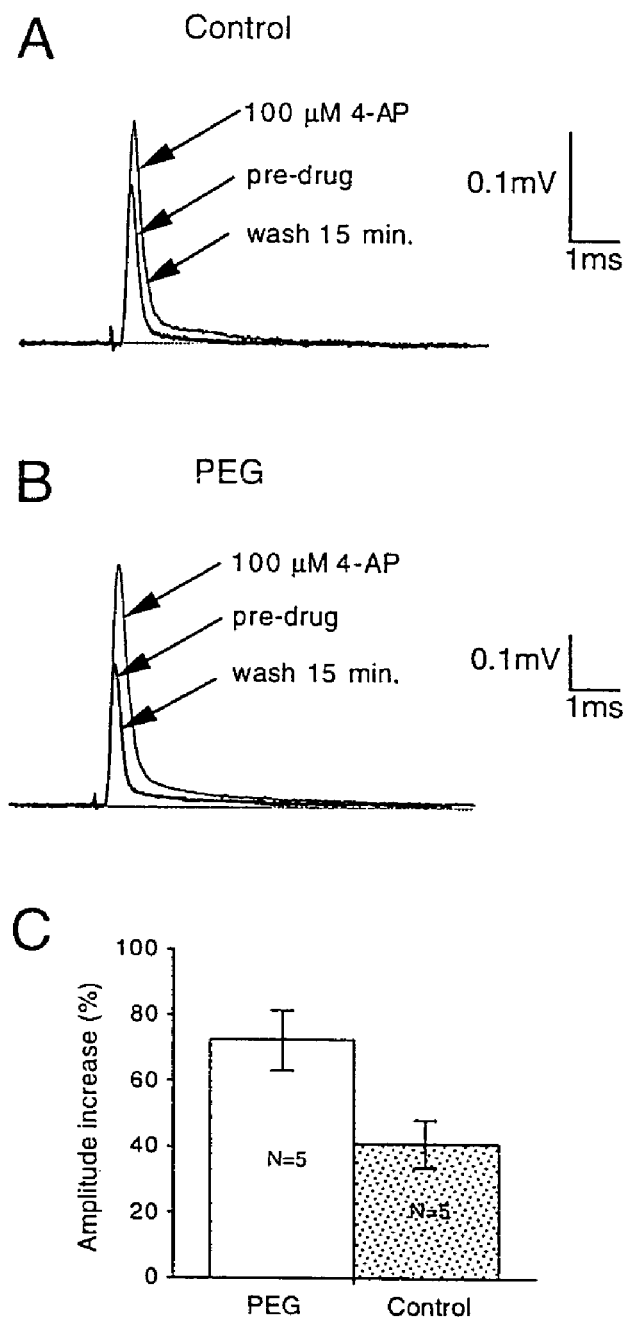
FIGS. 6A-6B depict electrophysiological recordings showing CAPs of control, and PEG/4-AP treated spinal cords.
In FIG. 6C, a bar graph of group data showing percent amplitude increase for 5 control and 5 PEG-treated spinal cords.

FIG. 6A shows the enhancement of the CAP in crushed (but untreated with PEG) spinal cord by 4-AP. In this individual record, the initial recovered CAP at 1 hour post injury is shown, and the enhanced CAP following 100 μM 4-AP treatment is superimposed upon it. Following documentation of the 4-AP enhanced CAP, the blocker was washed out, and the media in the central compartment was replaced with normal Krebs' solution. The CAP fell to pretreatment levels by 15 minutes and was indistinguishable from the original record. This final waveform is superimposed on the other two CAPs in FIG. 6A but cannot be discriminated from the pretreatment electrical record. In this single test, 4-AP reversibly enhanced the recovered CAP by about 40%.

FIG. 6B shows an identical test performed on a PEG-treated spinal cord, in which 4-AP was administered at 1 hour post PEG application. In this individual test, the second CAP was reversibly enhanced by about 70%.

Following the near doubling of the CAP, 4-AP was washed out as described, and the CAP fell to pretreatment levels as in controls (FIG. 6A).

FIG. 6C shows the group data, including 5 spinal cords in each group. The percent enhancement of the PEG-mediated recovery for the group data mirrors that discussed above for the individual experiments (about 70% enhancement in the experimental group; about 40% in the control group). This experimental enhancement was statistically significantly greater than that observed in the controls. ($p<0.05$, unpaired Student's t test)

Figure 7:
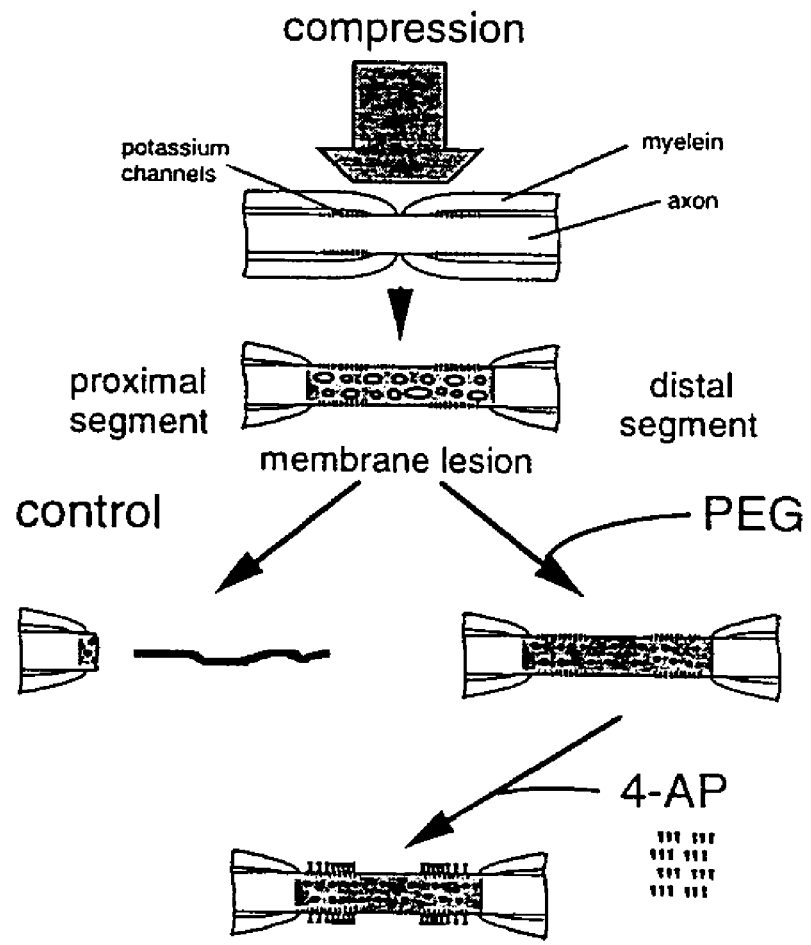
FIG. 7 depicts a proposed mechanism of the synergistic effect of PEG and 4-AP as more fully described in example 2. The membrane lesion obtained by mechanical compression is depicted by holes. Small arrowheads represent potassium channels.

Although not being limited by theory, FIG. 7 depicts a proposed mechanism of the synergistic effect of PEG and 4-AP. A severe mechanical compression of a myelinated axon is diagrammed at the top. Note that the myelin sheath envelops high densities of fast $K^+$ channels clustered at the paranodal region. Severe crush leads to an exposure of the potassium channels of the paranodal region by a withdrawal or collapse of the myelin lamella at this site [Shi, R. and Blight, A. R. (1996) *Neuroscience* 77:553-562]. Exposure of the voltage gated potassium channels after injury would elevate $K^+$ conductance further impeding conduction across this damaged portion of the membrane (gray region showing "holes" in the compromised membrane). In control preparations, partial to complete conduction block results from this localized disturbance of the axolemma, which may progress to complete separation of the axon and loss of the distal axonal segment by Wallerian degeneration (left side of FIG. 7). In PEG-treated axons (right side of FIG. 7), the membrane repair leads to preservation of injured axons as well as improvements in their conduction capabilities (gray regions; membrane holes now sealed). However, elevated $K^+$ conductance through $K^+$ channels that are still exposed at the site of repair in PEG-treated nerve fibers might still suppress conduction to some extent. Blockade of these channels with 4 AP (FIG. 7, small arrow heads; lower right) would be expected to reduce any outward $K^+$ conductance and thus enhance conduction.

Summary of Results

Within a few minutes after the application of the water-soluble polymer PEG, an immediate recovery of CAP propagation through the lesion occurred. The recovered CAP amplitude slowly increased with time to a peak of about 20% of the initial CAP amplitude. Moreover, this level of recovery was a.) always statistically significantly higher than control amplitudes, b.) observed at every time point tested, and c.) occurred in 100% of the experimentally treated spinal cords. It is clear that a topical application of PEG can immediately repair severe compression injury to the mammalian spinal cord leading to significant increases in functional recovery as defined by the enhanced capacity to propagate nerve impulses through the lesion. This report is the first to demonstrate PEG-mediated repair of crushed mammalian nervous tissue.

We have shown that a physiological, balanced media and the aforementioned PEG solution, is all that is required to produce functionally significant repair in mammalian spinal cords (see below). Moreover, in other experiments, where completely transected guinea pig spinal cords were fused with PEG, we have learned there was no specific PEG molecular weight critical to the process, having tested PEG solutions using 400, 1400, 1800, 2000, and 3700 daltons (unpublished observations).

In this physiological study, we have determined similarities and differences between the natural mechanisms of axonal repair and those mediated by PEG. First, a least squares linear regression analysis of pre- and postinjury CAP amplitudes suggests that PEG-mediated repair can occur across all levels of stimulus thresholds, reflecting axon diameters, as does the natural recovery process in untreated spinal cord strips. In other words, all spinal axons regardless of their caliber are equally susceptible to PEG mediated repair [see Shi, R. and Blight, A. R. (1996) *Neuroscience* 77:553-562 for a similar analysis of axonal recovery from compression injury]. The differences between natural repair and that produced by PEG application are more striking. First, this injury is very severe; 30% of control spinal cords never recovered any capacity to conduct CAPs during the 1 hour period of evaluation following injury. On the other hand, there was no instance where PEG did not initiate a measurable physiological recovery. On a more subtle level, there appears to be a slightly reduced CAP amplitude during the period of relative refractory in only PEG-mediated CAPs relative to control cords. One explanation for this observation may be that in control cords a severely compromised and dysfunctional population of axons may become completely nonfunctional, revealing more normal conduction properties in that population that survive the injury. PEG may rescue a portion of such severely compromised axons, recruiting them into the CAP, and perhaps accounting for its slightly different conduction properties.

The above-described in vitro evaluation of the anatomy of axonal repair following mechanical compression has revealed that a 2 minute application of PEG produced sealing of membrane lesions at the site of a standardized compression. Sealing was indicated by the exclusion of horseradish peroxidase uptake by injured fibers in the PEG-treated group compared to sham-treated spinal cords (to be reported elsewhere). Such immediate repair of membrane breaches sufficient to inhibit the uptake of large molecular weight dyes should also arrest or reduce permeabilization, allowing the nonspecific flux of ions across it. Although not being limited by theory, we believe it is this "sealing" behavior of PEG which both restores excitability and reverses anatomical dissolution of the nerve fiber.

This procedure may advantageously applied to treat severe, acute neurotrauma. In addition to immediate improvements in conduction, repair of crushed axons in peripheral nerves leading to a rescue of their distal segments would provide the added benefit of reducing atrophy or degeneration of target cells or so called "end organs." Moreover, PEG-mediated fusion of even transected axons could become a component of microsurgical grafting techniques since the conventional resection of peripheral nerve trunks prior to fascicular grafting exposes the severed tips of proximal and distal axonal segments, making them available for fusion.

EXAMPLE 3

Effect of PEG on Restoration of CAPs in Severed Spinal Cord Axons

This example demonstrates that severed spinal cord axons may be fused with PEG, thus allowing restored conduction of CAPs through the lesion site.

In Vitro Isolation of Spinal Cord

The spinal cord of adult female guineas pigs was isolated according to the protocol of example 1. After the cord was isolated, it was halved by midline sagittal division. The ventral white matter was separated from gray matter with a scalpel blade against a soft plastic block. Cords were maintained in continuously oxygenated Krebs' solution for at least an hour before mounting in the recording chamber. This was to ensure the recovery from dissection before each experiment was begun.

Double Sucrose Gap Recording Technique

The technique was followed according to the protocol in example 1. The central bath was connected to instrument ground. The entire chamber was mounted on a Peltier temperature control system, which also maintained the entire preparation at 37° C. Thermistors, in the chamber next to the spinal cord, constantly recorded and displayed the temperature. After mounting the spinal cord in the sucrose gap chamber, recorded CAPs and compound membrane (Gap) potentials usually stabilized with an hour [Shi, R. and Blight, A. R. (1996) J. of Neurophysiology, 76(3):1572-1579; Shi, R. and Blight, A. R. (1997) Neuroscience 77(2):553-562]; Shi, R. and Borgens, R. B. (1999) J. Neurophysiology, 81:2406-2414.

PEG Fusion Procedure

The basic methodology used to fuse spinal axons was as follows:

1). Restoration of typical physiological functioning of the isolated white matter strip removed to the recording chamber required about ½ to 1 hour of incubation time while immersed in oxygenated Krebs' at 37° C. Once both the Gap potential and CAP propagation were normal, the spinal cord strip was transected.

Figure 8:
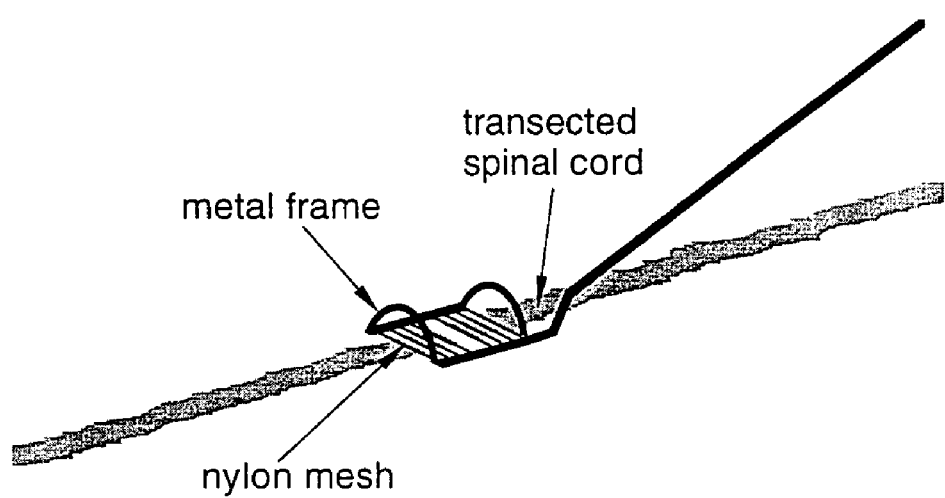
FIG. 8 depicts the laboratory device used to stabilize and hold the two segments of the spinal cord together during fusion.

2). The spinal cord strip was completely severed with a laboratory fabricated cutter (a shard of a razor blade attached to an applicator stick), and the two ends of the spinal cord were observed to be separated by a gap of about 0.5-1 mm with a stereomicroscope. The spinal cord was transected within the middle of the central compartment of the recording chamber. Stimulation and recording were continued during this operation. Following transection, the two ends of the cord segments were "pushed together," i.e., abutted tightly using a watchmaker forceps and a laboratory fabricated device that applied gentle pressure on one segment of the spinal cord strip pressing and holding it against the other. The device was mounted on a micropositioner, and contacted the spinal cord parenchyma with a strip of nylon mesh stretched across two metal bands (FIG. 8). The metal frame of the device never contacted the spinal cord tissues during use. Only the nylon mesh was in contact with the tissue. Several methods to accomplish stabilization during the fusion process were tested, the most effective involved first lightly placing the mesh onto the intact cord. Once this was accomplished, the spinal cord strip was completely transected, with a gap appearing between the two segments which were then repositioned as discussed above.

3). Various solutions of PEG (1400, 1800, 2000, and 3500 daltons, 50% by weight in distilled water) were applied by pressure injection through a micropipette in preliminary experiments (data not shown), while the data reported here exclusively utilized PEG of having a molecular weight of about 1800 daltons. A vital dye was added to the PEG solution to monitor its application to the lesion site as a continuous stream about 0.5 mm wide and continuing for about 1-2 minutes. The PEG was applied to one side of the lesion, washed transversely across it, and was removed by constant aspiration on the other side using a second suction pipette.

4). During the PEG application, a continuous stream of oxygenated Krebs' solution was maintained. The electrophysiological properties of the spinal cord following PEG treatment was monitored continuously for approximately 1 hour.

Results

Figures 9A, 9B, 9C, 9D, 9E, 9F, 9G, 9H, 9I:
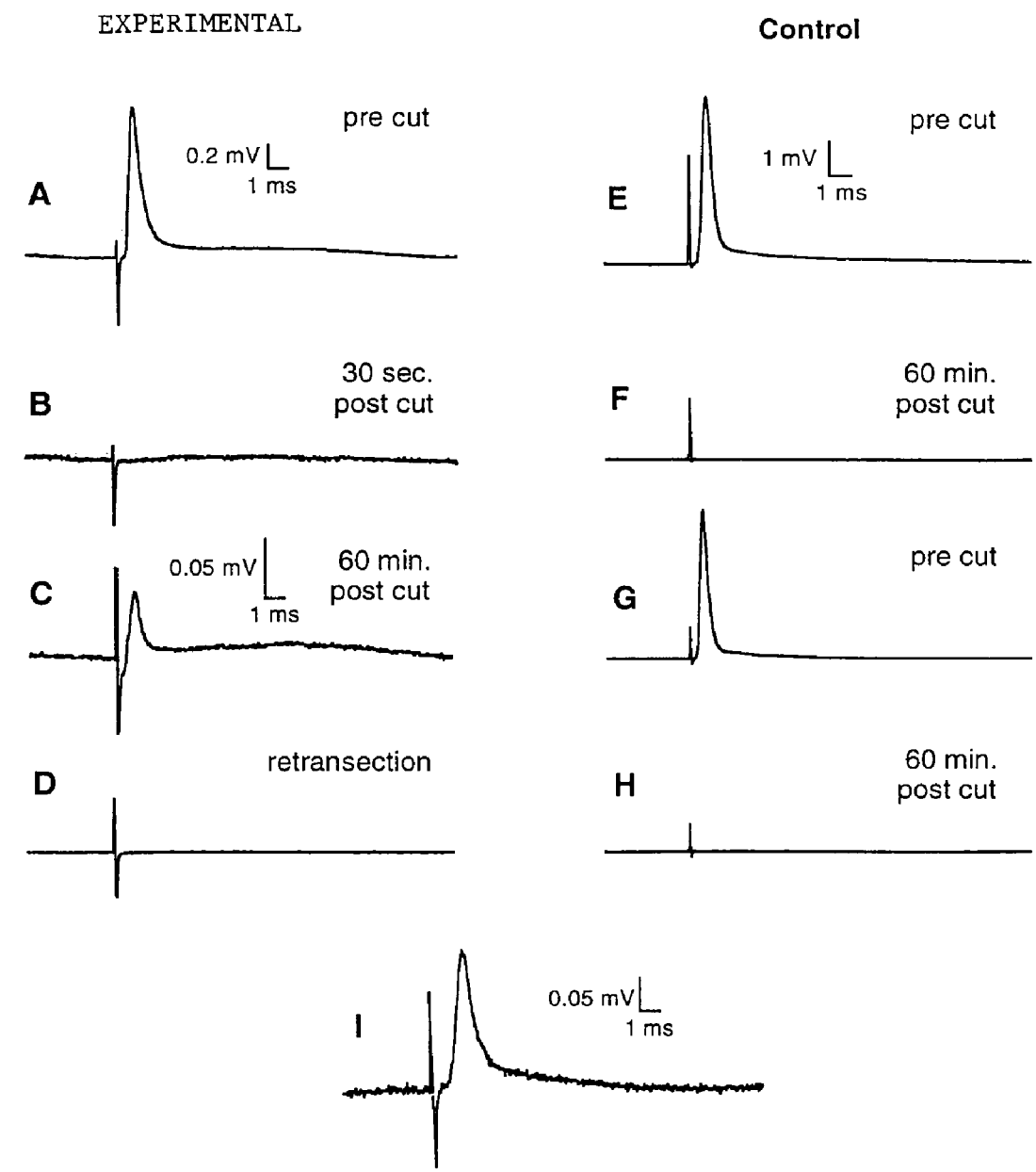
FIGS. 9A-9I depict electrophysiological recordings in adult guinea pig spinal cords at 37° C.
Figures 10A, 10B, 10C, 10D:
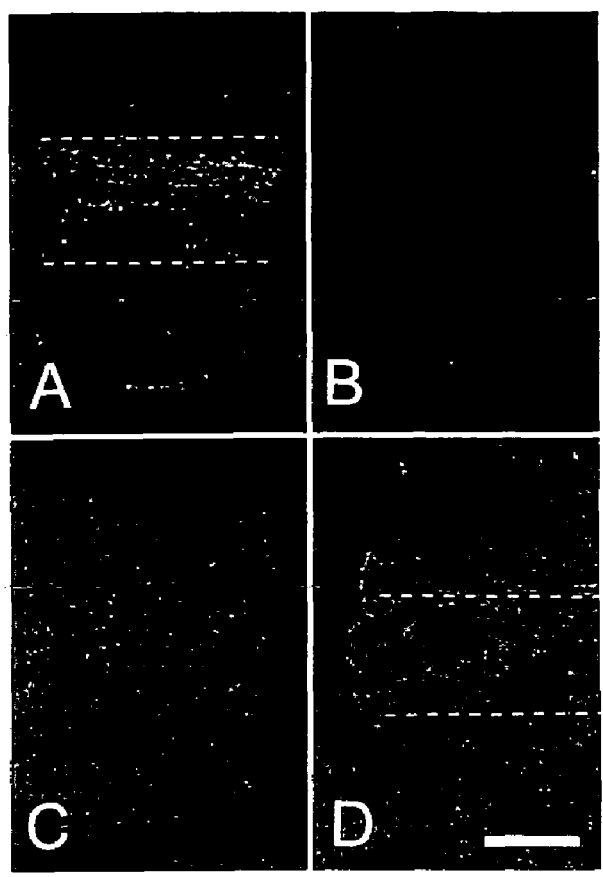
FIGS. 10A-10D show fluorographs of adjacent transected surfaces of a transected strip of guinea pig spinal cord white matter facing each other across a gap. About 1.5 μl of FR was injected into segment A, and revealed using excitation/barrier wavelengths of 545/590 nm, respectively, in darkfield. The adjacent segment in B, illuminated with the same excitation and barrier filter combination, was injected with FE. Note the absence of FR filled axons in B. Images C and D are identical views to A and B, only illuminated with excitation/barrier wavelengths of 495/515 nm sufficient to reveal only the FE labeled axons seen in D. Note that in these control preparations, as in all unfused regions of spinal cords, dye labeled axons are never visualized in the segment of spinal cord not originally injected. The dashed lines show the approximate boundaries of a projection of dye labeled axons from their site of injection (out of the photographic field) to the plane of transection. Scale bar for A, B, C, and D=500 μm.

Typical CAPS were recorded in response to stimulation, and were completely eliminated following transection of the cord between the stimulation and recording electrodes in every spinal cord strip tested (FIGS. 9A and 9B). The recovery of CAPs was often observed within 5-15 minutes following PEG application and continued for up to 60-80 minutes, at which time physiological recordings were discontinued (FIGS. 9C and 9I). Since the conduction of CAPs across the plane of transection does not occur in severed spinal cords, a fusion was defined as successful if a restored CAP was detected demonstrating properties of latency and stimulus threshold. In preliminary experiments, we learned that the success of an attempted fusion depended on the alignment and the care taken during abutment of the spinal cord segments prior to PEG application. The ends of the strips cannot be too tightly forced together or this produces more injury to the spinal cord. They cannot be too loosely abutted or fusion of the axolemmas will not take place (see below). All 20 of the attempted fusions reported here were successful. Recovered CAPs were on the order of 5% of the peak magnitude of the original pre-transection CAPs. Note that the computer managed data acquisition techniques used in to obtain physiological recordings shown in FIGS. 9A-9I have been previously reported [Shi, R. and Blight, A. R. (1996) J. of Neurophysiology, 76(3):1572-1579; Shi, R. and Blight, A. R. (1997) Neuroscience 77(2):553-562]

Table 1 below provides the quantitative data derived from an evaluation of 20 successful fusions using 1800 dalton PEG. In preliminary experiments, we also achieved identical, functional fusions in a few cases using 1400, 2000, and 3500 dalton PEG (data not shown).

TABLE 1

Characteristics of 20 successful fusion of mammalian spinal cord axons utilizing 1800 dalton PEG.

| | AP amplitude | | | | | peak latency (ms) | | | | | ½ height duration (ms) | | | | |
|---|---|---|---|---|---|---|---|---|---|---|---|---|---|---|---|
| exp.#[1] | pre[2] | post[3] | (%)[4] | SEM[5] | Range[6] | pre | post | (%) | SEM | range | pre | post | (%) | SEM | range |
| 20 | 2.44 | 0.44 | 4.61 | 2.83 | 0.2-58.0 | 0.93 | 1.05 | 114.5 | 8.71 | 26-227 | 0.63 | 0.53 | 85.5 | 6.45 | 36-156 |

[1]Total number of fusions carried out at 37° C.
[2]Data obtained before transection.
[3]Data obtained after PEG-mediated fusion.
[4]Mean percent recovery after fusion
[5]Mean standard error after fusion.
[6]Range of data.

We performed a series of control procedures to insure that restored CAP conduction was indeed a function of restored axonal integrity and not produced as an artifact by some alternate means of conduction. For example, CAPs were not conducted across the plane of transection if: 1). subthreshold stimulation was applied to PEG fused cords (20 cases), 2). the original fusion site was again transected with the cutting device (6 cases, FIG. 9 D), 3). spinal cord segments were closely abutted in the stream of Krebs's solution, but PEG was not applied (5 cases, FIGS. 9E and 9F), and 4). PEG was applied to poorly abutted segments (5 cases, FIGS. 9G and 9H).

EXAMPLE 4

Effect of PEG on Anatomical Continuity of Severed Axons

This example illustrates that PEG fuses and repairs severed axons such that intracellular fluorescent dyes may diffuse across the original transection. Moreover, the restored anatomical continuity is shown to be correlated with the restored ability to conduct CAPs.

Tract Tracing with Intracellular Fluorescent Probes

Intracellular injections of two fluorescently decorated-dextrans were used to evaluate the integrity of formerly transected nerve fibers by procedures previously described [Borgens, R. B. and Bohnert, D. M. (1997) *Exp. Neurol.* 145:376-389]. Briefly, injections of about. 1-1.5 μl of one tracer, tetramethylrhodamine dextran or Fluororuby (FR, 8000 dalton, Molecular Probes Inc.), was made to one segment of the fused cord, approximately 4-6 mm from the original plane of transection. This label was observed with excitation/barrier wavelengths of 545/590 nm respectively, in darkfield. Likewise, a second and similar injection of another tracer, FITC conjugated dextran or Fluoroemerald (FE, 8000 dalton, Molecular Probes, Inc.) was made to the opposite segment and observed with excitation/barrier wavelengths of 495/515 nm, respectively. Approximately 12-14 hours later the cords were immersion fixed in 5% glutaraldehyde/0.01% paraformaldehyde. This time period allowed the intracellular markers to diffuse throughout axons. During this incubation period, a continuous flow of oxygenated Krebs' solution was maintained through the central compartment of the recording chamber, which helped to eliminate any extracellular diffusion of the dye. Longitudinal horizontal sections (about 15-30 μm) of the spinal cord strips were made on either a freezing microtome or the tissue was imbedded in paraffin for sectioning by conventional histological technique. Each of these dyes was viewed independently using the appropriate barrier and filter combinations in fluorescent darkfield. We performed these operations on 8 PEG-treated, and fused spinal cord strips. Additional control procedures were performed on 5 spinal cord strips to insure that dye did not travel into the opposite segment of the cord from where it was injected. This involved injecting the two dyes into cord segments as previously described; however, these segments were tightly abutted but not fused with PEG.

In another 5 PEG-treated spinal cord strips, high resolution light microscopy was used to evaluate the plane of fusion. These fixed strips of spinal cord were cut to a length of about 5 mm containing the fusion plane, embedded in plastic by conventional methods, sectioned at 0.5-1 micron on an ultramicrotome, and stained with 1% toluidine blue. Microscopic images were captured directly to a Dual Pentium PRO PC from an Olympus Van Ox Universal microscope fitted with an Optronics DEI-750 3 CCD video camera system.

Results

The anatomical continuity of axons that had been fused at the plane of transection was correlated with the restored ability to conduct CAPs in 13 spinal cords. This was determined by the intracellular diffusion of the two different fluorescent dyes across the lesion site in 8 cords and in 5 additional cords by conventional microscopy of plastic imbedded sections. Axons filled with the different dyes were examined independently of each other by fluorescence microscopy with different excitation and barrier filter combinations in darkfield. FIGS. 10A-10D are typical of all 5 control preparations (cord segments tightly abutted but without PEG application) in which the potential of the dye to diffuse from one segment to the other by an extracellular pathway was examined. In all controls, a dye injected into axons of one segment was never observed within axons of the opposite cord segment. This was in part due to the small dye volume injected (about 1.5 μl) coupled to a continuous flow of media through the central compartment of the recording chamber maintained during the entire procedure. This eliminated the spread of dye by an extracellular diffusion path.

Figures 11A, 11B, 11C, 11D, 11E, 11F:
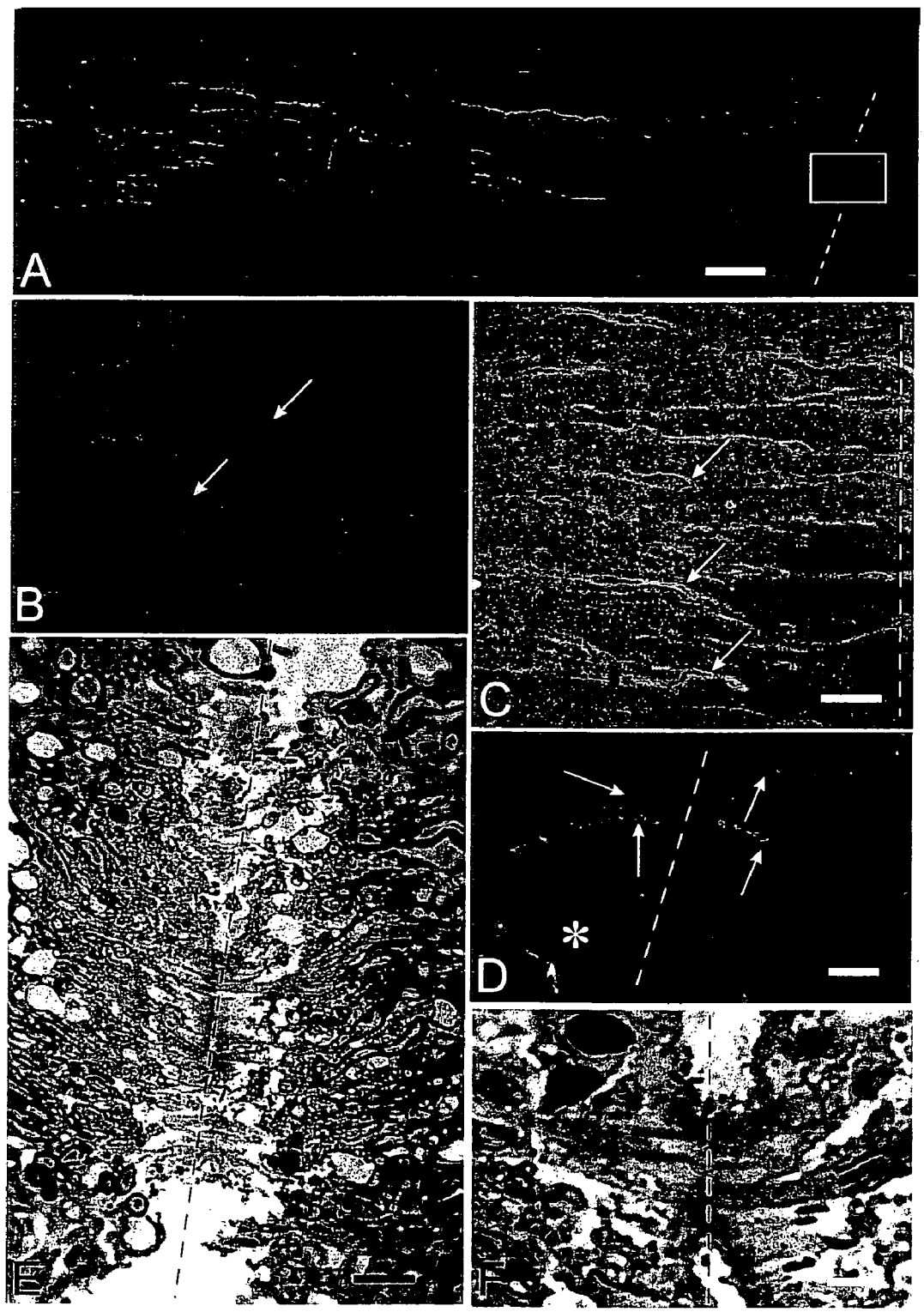
FIGS. 11A-11F depict fluorographs of PEG-fused regions of four separate spinal cords strips that were initially transected, treated with PEG and injected with fluorescent dyes as more fully described in example 4. The approximate plane of fusion is marked with a dashed line. An FR-labeled projection is show in FIG. 11A at low magnification. The rectangle in FIG. 11A circumscribes the region shown in FIG. 11B at higher magnification. The arrows in FIG. 11B depict sites where one axon segment appeared to be fused to two others.

In both control and experimentally fused cords, unfused axons retracted back from the transection plane for a variable distance (50 μm-0.5 mm), their terminal clubs or endbulbs clearly visible (FIG. 11C). The plane of transection was identifiable in PEG-fused cords as a transverse series of gaps and holes interspersed with well-fused regions of spinal cord parenchyma (FIGS. 11A, and 11D-11F). We believe such gaps result from partial separation of the fused segments during handling prior to fixation as well as incomplete perfusion of the cord with PEG. Since PEG probably fuses some non-neuronal cells as well as neuronal processes, the original transection plane in well fused expanses of spinal cord was nearly undetectable with fluorescent microscopy sufficient for visualizing the two intracellular dyes. However, blue-violet fluorescent illumination induced some spinal cord auto fluorescence which could reveal the fusion plane in these regions as a very fine "seam".

In all 8 cords in which tract tracing was performed, a recovered CAP was documented. In 6 of these, fibers filled from either end of the cord traversed the fusion plane into the adjacent segment. In 2 of these 6 strips, only fibers filled with FR crossed the lesion, the FE labeled segments being poorly filled. It was common to observe the terminal ends of unfused axons within a few micrometers of fused axons adjacent to them which filled along their lengths across the original transection (FIG. 11C). In one case we observed axons to have fused to two or more others, producing a tangle of nerve fibers within the transection gap (FIGS. 11A and 11B). This tangle of fibers could also be traced to the opposite spinal cord segment. Additionally, note that the approximate site of dye injection in FIG. 11A is to the left of the image and out of the field of view. In three of the five cords evaluated by high resolution light microscopy, unmyelinated expanses of myelinated axons fused at the original plane of transection (FIGS. 11E and 11F). In these regions membrane and myelin debris could also be seen in the gap surrounding the reattached fibers. Furthermore, in FIG. 11E, the two, re-apposed ends of the white matter strip show continuity over a length of apposition in the middle of the frame. The plane of transection (dashed line) is clear from the slight gaps that remain between the ends of the strip at the top and bottom of the figure, which continue across the whole width of the tissue in the rest of the section (visible at lower magnification).

Summary of the Results

Our data show that a water soluble polymer, PEG, can be used to rapidly reconnect the severed halves of spinal axons within completely severed strips of isolated spinal cord white matter. This fusion has been documented by both anatomical and physiological means. In the former, fluorescent intracellular markers were injected into each spinal cord segment. In 6 cases of 8, axonal continuity across the plane of fusion was demonstrated. By searching the fusion plane in plastic embedded sections, unambiguous evidence of axonal fusion in three of five additional spinal cord strips was detected.

In all five control spinal cords, the intracellular label was never observed in the opposite cord segment from where it was injected. This was largely due to the elimination of an extracellular diffusion pathway from the site of injection to the opposite cord segment by the flowing medium in the central compartment and the separation of compartments by the sucrose gap "boundaries". Furthermore, the presence of numerous terminal clubs of transected but unfused axons adjacent to well-labeled axons crossing the transection plane provided additional anatomical evidence that true fusion of severed proximal and distal axon segments had taken place.

The immediate restoration of CAP propagation across the transection plane in completely severed spinal cords following PEG treatment could only have occurred coincident with the functional reconnection of proximal and distal segments of axons. In control spinal cords, CAP conduction did not reappear following tight abutment of the severed segments when PEG was not applied. Furthermore, CAP conduction did not reappear in segments that were poorly abutted by design and also treated with PEG. Thus, PEG itself does not provide some sort of substrate permitting CAP conduction. We conclude that a topical application of PEG indeed functionally reunites severed mammalian nerve processes. This observation compliments and extends our demonstration that topically applied PEG can repair guinea pig spinal cords severely crushed by a standardized procedure leading to an immediate recovery of action potential propagation through the lesion [Shi, R. and Borgens, R. B. (1999) J. Neurophysiol. 81:2406-2414].

EXAMPLE 5

In Vivo Effect of PEG on Restoration of the CTM Reflex in Guinea Pigs with Crushed Spinal Cords This example illustrates that in vivo treatment of crushed guinea pig spinal cords restores the CTM reflex.

Surgery and Anesthesia

A total of 51 adult (300 gm) guinea pigs were used in two separate experiments. Guinea pigs were anesthetized with an intramuscular injection of 100 mg/kg ketamine HCL, and 20 mg/kg xylazine, and the spinal cord was exposed by dorsal laminectomy [Borgens, R. B., et al. (1986) J. Comp. Neurol. 250:157-167; Borgens, R. B., et al. (1990) J. Comp. Neurol. 296:634-653]. Subsequently, a constant displacement 15 second compression of the spinal cord was performed using a modified forceps possessing a détente [Blight, A. R. (1991) J. Neurolog. Sci. 103:156-171]. In this experiment, the lesioning procedure had previously been calibrated to produce an immediate and total loss of CAP conduction through the injury and behavioral functioning of the cutaneous trunci muscle reflex (see below). For some SSEP measurements, or to sedate animals for behavioral testing and videotaping, guinea pigs were injected with 0.1 cc $Na^+$ Pentobarbital, 50 mg/ml. Surgery and functional testing were carried out under protocols approved by the Purdue University Animal Care and Use Committee, in accordance with Federal, State, and University guidelines governing animal use in research.

PEG Application

An aqueous solution of PEG (either 400 or 1800 daltons, 50% by weight in distilled water) was applied with a pipette to the exposed injury for two minutes in experimental animals, and then removed by aspiration. As in prior in vitro experiments [Shi, R. et al. (1999) J. of Neurotrauma 16:727-738; Shi, R. and Borgens, R. B. (1999) J. Neurophysiology 81:2406-2414], no difference in the response to these two solutions was detected, so these data are pooled in this report. The site of PEG application was immediately lavaged with isotonic Krebs' solution (124 mM NaCl, 2 mM KCl, 1.24 mM $KH_2PO_4$, 1.3 mM $MgSO_4$, 1.2 mM $CaCl_2$, 10 mM dextrose, 26 mM $NaHCO_3$, and 10 mM sodium ascorbate), and any excess PEG and/or Krebs' solution removed by aspiration. Although PEG was not applied to the injury in sham-treated animals, the site was lavaged with Krebs' solution which was subsequently removed by aspiration. The wounds were closed, and animals kept warm until awaking with heat lamps. Guinea pigs were housed individually and fed ad libidum.

In the first experiment, we attempted to repeat the remarkable complete reversal of functional loss within minutes of severe spinal injury as observed in in vitro trials [Shi, R. et al. (1999) J. of Neurotrauma 16:727-738; Shir, R. and Borgens, R. B. (1999) J. Neurophysiology 81:2406-24141. Thus, PEG was applied within about 15 minutes of spinal cord compression (experimental n=14, control n=11). In the second experiment, PEG application was delayed for about 8 hours (experimental n=11, control n=11). The former groups were evaluated for about 4 days, and the latter, for about 1 month, after PEG application. In both experiments, documentation of CTM behavior was combined with physiological recording.

An additional 4 PEG-treated animals were followed for 1 day post injury at which time their spinal cord was again exposed at the site of the original injury and crushed again at this location using the same technique as reported above.

Behavioral Analysis of the Cutaneus Trunci Muscle (CTM) Reflex

Figures 12A, 12B, 12C, 12D:
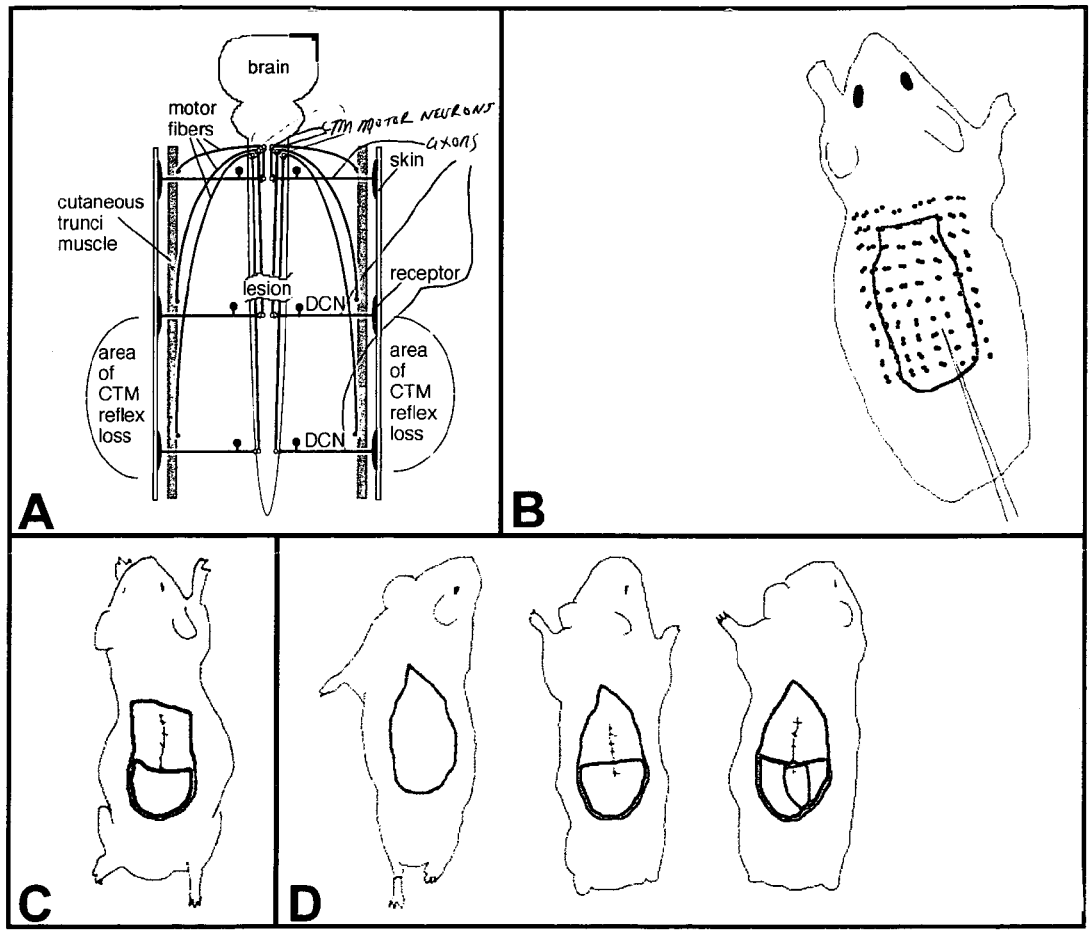
FIG. 12A is a diagram of the sensory and motor components of the cutaneous trunci muscle (CTM) reflex of the guinea pig as more fully discussed in Example 5.
FIGS. 12B-12D depict drawings of captured and superimposed video images of a guinea pig during a period of CTM stimulation with a monofilament probe. Two video frames were superimposed to show the position of the dots prior to stimulation (black dots) and $\frac{1}{25}^{th}$ second after stimulation [red dots; see also Blight et al., (1990) *J. Comp. Neurology* 296: 614-633; and Borgens, R. B. and Shi, R. (1999) *J. Faseb* (in press)].

The CTM behavior is observed as a corrugated rippling of backskin in response to light tactile stimulation (FIG. 12B). The behavior is dependent on afferent sensory projections organized as a long tract of axons in each ventral funiculus of the spinal cord, just lateral to the spinothalamic tract [Blight, A. R., et al. (1990) J. Comp. Neurol. 296:614-633; Thierault, E. and Diamond, J. (1988) J. Neurophys. 60: 446-463; Thierault, E. and Diamond, J. (1988) J. Neurophys. 60: 463-477].

Specifically, FIG. 12A shows a diagram of the sensory and motor components of the CTM reflex of the guinea pig. Sensory receptors in backskin project afferent axons into each thoracic segment on both sides via the dorsal cutaneous nerves (dcn). These enter the spinal cord and synapse on second and third order neurons which project their axons (red) to the thoracocervical junction. These tracts of ascending nerve fibers are located on each side of the spinal cord within the ventral funniculus, lateral to the spinothalalmic tract. These ascending axons synapse on bilaterally located pools of CTM motor neurons located between T-1 and C-6. Motor fibers (blue) exit the spinal cord on each side as a component of the brachial plexus and innervate the cutaneous trunci muscle of the skin. Note that a spinal cord lesion extending across both sides of the cord compromises ascending tracts, producing a region of backskin areflexia on both sides below the level of the injury. In this region of skin, tactile stimulation no longer elicits skin rippling.

The reflex is bilaterally organized as segmental receptive fields, displays little supraspinal control, and is usually permanently lost following severe spinal injury producing a bilateral region of areflexia below the level of the lesion [Borgens, R. B., et al., J. Comp. Neurol. 296:634-653; Blight, A. R., et al. (1990) J. Comp. Neurol. 296:614-633; Thierault, E. and Diamond, J. (1988) J. Neurophys. 60: 446-463; Thierault, E. and Diamond, J. (1988) J. Neurophys. 60: 463-477] (FIGS. 12 A and 12C). In such cases, recovery of the CTM reflex in response to tactile or electrical stimulation within the region of areflexia is usually not observed for the life of the animal. The anatomy, physiology, and character of the CTM behavior—both normal and in response to lesioning—has been reported in both rat and guinea pig [Blight, A. R., et al. (1990) *J. Comp. Neurol.* 296:614-633; Thierault, E. and Diamond, J. (1988) *J. Neurophys.* 60: 446-463; Thierault, E. and Diamond, J. (1988) *J. Neurophys.* 60: 463-477].

To visualize and quantify the CTM behavior, a matrix of dots was marked onto the backskin of the animal. When the shaved backskin of sedated guinea pigs was touched with a monofilament probe, the backskin in uninjured or intact receptive fields contracted in response to the tactile stimulation (FIG. 12B). The boundary between responsive and unresponsive backskin was marked onto the backskin with a marker (shown in green) while the entire study period was videotaped from a platform mounted camera above. Probing outside this area does not evoke skin contraction.

Animals were arranged on a background grid to facilitate the registration of successive video images. Video images were acquired to an Intel® Dual Pentium® Pro computer. Superimposing of images, the coloring of receptive field boundaries made on the backskin of the animals during CTM testing, and the general management of video images was performed using Adobe® Photoshop® software. Final Plates were constructed with Microsoft® Powerpoint® software and printed on an Epson Stylus Color 800 printer. Quantitative planimetry of the unit area of receptive fields—or regions of behavioral loss and recovery—was carried out using IP Lab Spectrum™ software.

Statistics

The Mann Whitney, two-tailed test was used to compare the means of the data derived from experimental and sham-treated groups. To compare the proportions between groups, Fishers exact test was used. All tests were performed using INSTAT software.

Results

The standardized injury produced a similar loss of CTM functioning in experiments testing the response to the immediate application of PEG and experiments testing the response to the delayed application of PEG. The percent loss of CTM receptive fields (FIG. 12C) was not statistically different between either of the two experiments or between sham-treated and PEG-treated guinea pigs in either experiment ($P>0.4$, Student's t test, two-tailed). Only one animal died during the course of this study.

Behavioral Loss and Recovery of the CTM Reflex

In both experiments, 19 of the 22 sham-treated animals did not recover CTM functioning, as seen in Tables 2 and 3.

TABLE 2

Percent recovery of the CTM[1] reflex in adult guinea pigs after immediate treatment with PEG.

| | Day 1 | | | | Day 4 | | | | |
|---|---|---|---|---|---|---|---|---|---|
| | Animal Number | $\bar{X} \pm SEM$[2] | Range[3] | Stat[4] | Animal Number | $\bar{X} \pm SEM$ | Range[3] | Stat[5] | Stat[4] |
| Control | 0/11 | 0 | 0 | 0.0005 | 2/11 | 0.18 ± 1.9 | −15-11 | 0.015 | 0.006 |
| PEG-Treated | 10/14 | 6.2 ± 1.4 | 0-15.2 | | 10/14 | 13.8 ± 3.8 | 0-42.1 | | |

[1]The increase in the area of backskin regaining sensitivity to tactile stimulation is given as a percent of the total region of CTM behavioral loss. All unit areas in cm[2] were calculated by planimetry from captured video images.
[2]$\bar{X}$ = Mean % Recovery of the CTM Reflex and Standard Error of the Mean
[3]The range of the control data set at 4 days includes the percent increase in the area of CTM loss which is given as a negative number.
[4]P value: proportion of recovered and unrecovered animals evaluated with Fishers' exact test, two-tailed.
[5]P value: means compared with Mann Whitney, two tailed test.

TABLE 3

Percent recovery of the CTM[1] reflex in adult guinea pigs after delayed treatment with PEG.

| | Day 1 | | Day 3 | | 2 Weeks | | 1 Month | |
|---|---|---|---|---|---|---|---|---|
| | Animal Number | $\bar{X} \pm SEM$[2] | Animal Number | $\bar{X} \pm SEM$ | Animal Number | $\bar{X} \pm SEM$ | Animal Number | $\bar{X} \pm SEM$ |
| Control | 0/11 | 0 | 1/11 | 2.8 ± 2.8 | 1/11 | 2.8 ± 2.8 | 1/11 | 2.8 ± 2.8 |
| PEG-Treated | 9/11 | 11.8 ± 2.9 | 9/11 | 11.9 ± 2.9 | 10/11 | 15.3 ± 3.3 | 10/11 | 19.5 ± 3.02 |
| Statistic | 0.0002[4] | NA[6] | 0.002[4] | 0.009[5] | 0.0003[4] | 0.003[5] | 0.0003[4] | 0.0008[5] |

[1]The increase in the area of backskin regaining sensitivity to tactile stimulation is given as a percent of the total region of CTM behavioral loss. All unit areas in cm[2] were calculated by planimetry from captured video images.
[2]$\bar{X}$ = Mean % Recovery of the CTM Reflex and Standard Error of the Mean
[3]The range of the control data set at 4 days includes the percent increase in the area of CTM loss which is given as a negative number.
[4]P value: proportion of recovered and unrecovered animals evaluated with Fishers' exact test, two-tailed.
[5]P value: means compared with Mann Whitney, two tailed test.
[6]Statistical comparison of means not applicable to this data set.

During the first experiment, CTM functioning actually worsened by day 4 in two control animals (the region of CTM loss increased by 2% and 15% respectively; Table 1). In contrast, CTM functioning recovered in 10 of 14 PEG-treated animals in the first experiment (about 80%; FIG. 12D, Table 2), and in greater than about 90% of experimental animals in the second experiment. In all PEG-treated animals, the restored region of CTM competent backskin was observed within the first day following treatment and continued to increase in size with time (Tables 2 and 3). For example, the average unit area of backskin recovering CTM sensitivity nearly doubled from about 12% (day 1) to about 20% by 1 month post application in the second experiment (Table 3). Both the increased proportion of animals recovering CTM function, and the average increase in the areas of recovered CTM competent backskin in response to PEG, was statistically significant (Table 2 and 3).

EXAMPLE 6

In Vivo Effect of PEG on Conduction of Somatosensory Evoked Potentials Through Crushed Guinea Pig Spinal Cord This example demonstrates that in vivo application of PEG to an injured spinal cord allows for conductance of evoked CAPS, known as somatosensory evoked potentials (SSEPs), through the region that was injured.

Physiological Recording of SSEPs

A pair of subdermal electrodes stimulated nerve impulses from the tibial nerve of the hindleg (stimuli trains in sets of 200 at 3 Hz; stimulus amplitude less than or about equal to 3 mA square wave, 200 µs duration). Evoked volleys of CAPs were conducted into the spinal cord, projected to, and recorded from, the sensory cortex of the brain. Recording of the nerve impulses at the brain employed a pair of subdermal electrodes located above the level of the contralateral cortex with reference electrodes located in the ipsilateral pinna of the ear. Stimulation, recording, signal averaging, and the computer management of this physiological data utilized a Nihon Kohden Neuropak 4 stimulator/recorder and Power-Mac G3 computer.

Figures 13A, 13B, 13C, 13D:
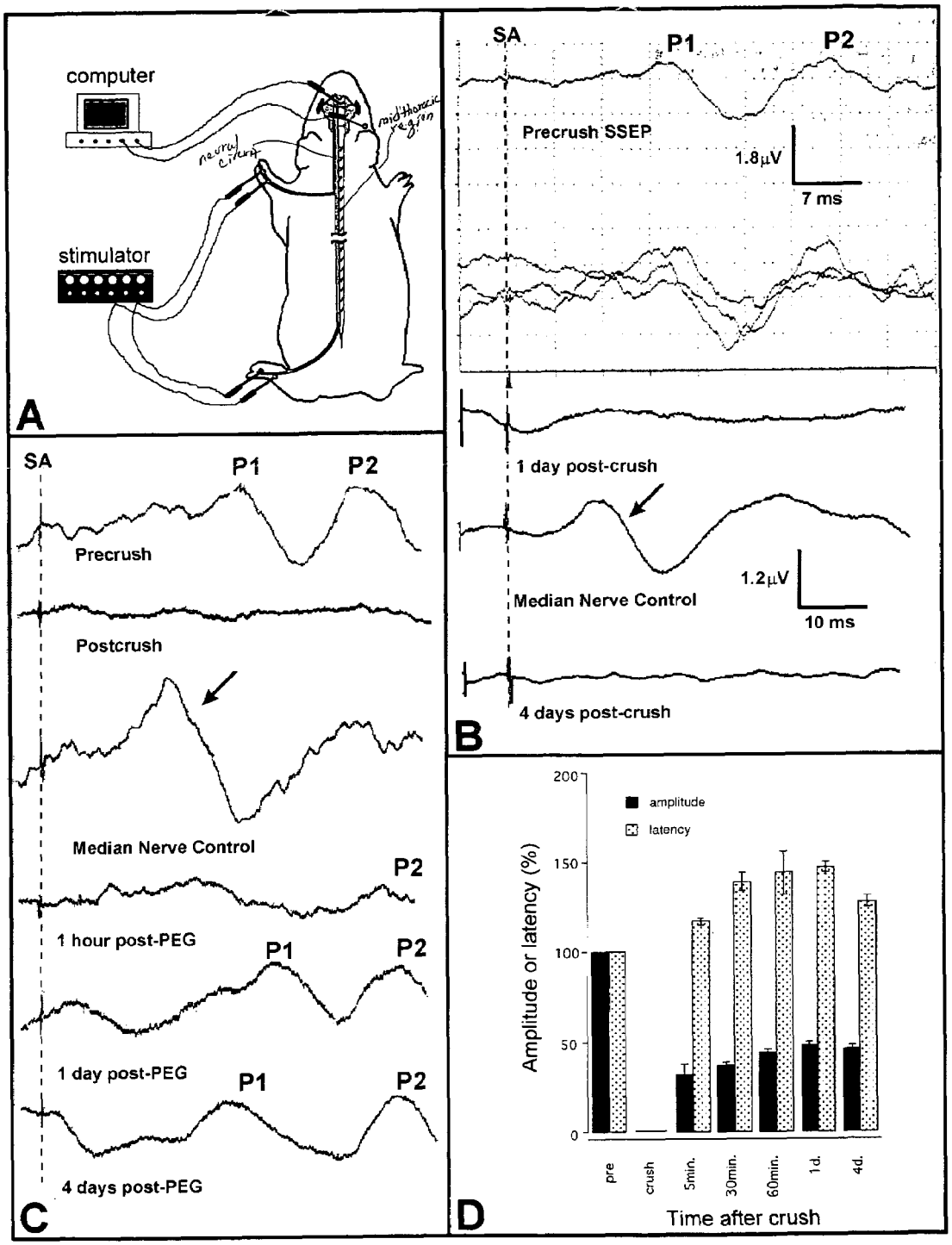
FIG. 13A depicts an experimental setup used in the examples. Nerve impulse pathways were interrupted by crushing the spinal cord in the midthoracic region (red circuit). A control procedure demonstrated that a failure to detect SSEPs was due to a failure of ascending nerve impulse conduction through the lesion by stimulation of a neural circuit unaffected by the injury (blue circuit).
FIGS. 13B-D depict SSEP electrical recordings. The top panel of FIG. 13B shows a complete somatosensory evoked potential (SSEP) electrical recording in an uninjured guinea pig. The lower panel of FIG. 13B shows the three individual traces used to produce the averaged signal seen in the top panel. SA=stimulus artifact; P1=first arriving SSEP (latency=about 18 ms); P 2=late arriving potentials (latency=about 34 ms). The arrow in the lower panel of FIG. 13B points to a typical SSEP in response to median nerve stimulation, showing interruption in conduction was due to the lesion. Below the median nerve control response, an SSEP in response to tibial nerve stimulation 4 days post-injury is depicted.

Measurements of SSEPs were carried out in every animal prior to spinal cord injury (FIGS. 13A-13D). In all animals (at any test period), the failure to record an SSEP following stimulation of the tibial nerve was further confirmed to be due to a lack of conduction through the spinal cord lesion by a control test carried out on the same animal. In this procedure, the medial nerve of the forelimb was stimulated, initiating evoked potentials in a neural circuit unaffected by the crush injury (FIGS. 13A-13C). To perform this test, recording electrodes were left in place while stimulating electrodes were relocated to stimulate the median nerve using identical parameters of stimulation.

Statistics

The Mann Whitney, two-tailed test was used to compare the means of the data derived from experimental and sham-treated groups. To compare the proportions between groups, Fishers exact test was used. All tests were performed using INSTAT software.

Results

Physiological Measurements of Conduction through the Spinal Cord Injury

Figures 14A, 14B, 14C:
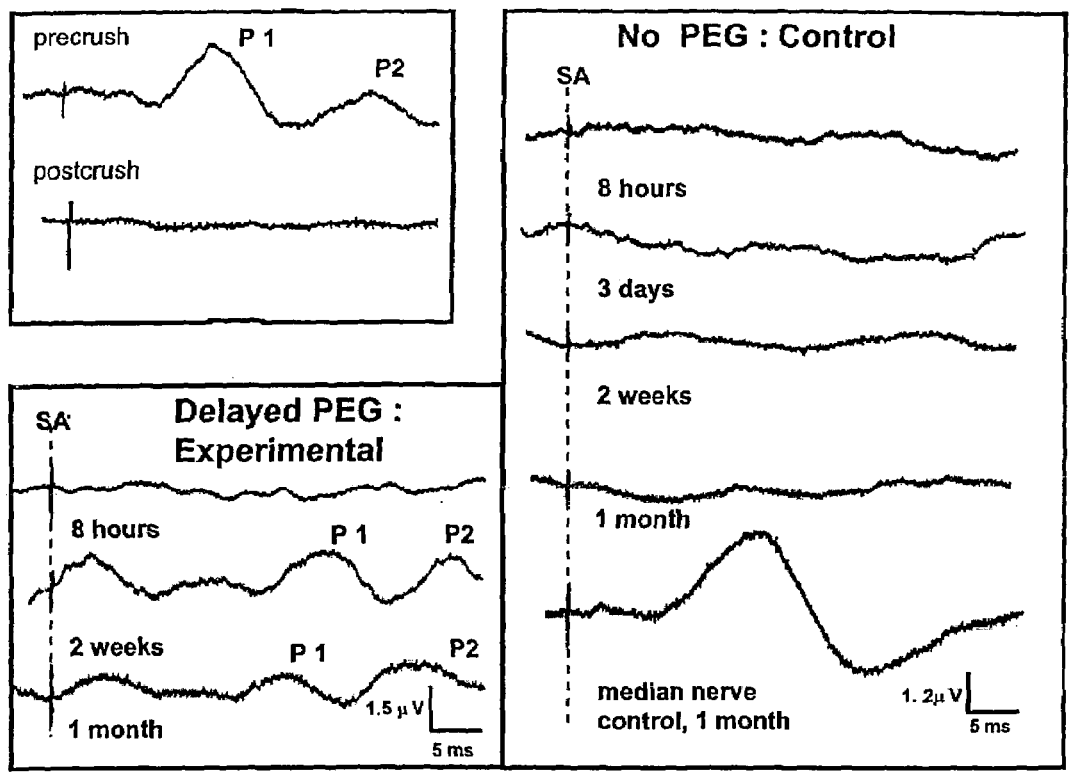
FIGS. 14A-14C depict SSEP electrical recordings in control guinea pigs and guinea pigs treated with PEG at various times postcrush.

Physiological measurements of SSEP conduction were performed in every animal prior to spinal cord injury and within 5-15 minutes after surgery (FIGS. 13B and 13C; FIGS. 14A-14C) to provide a basis for later comparison. In the uninjured animal, SSEPs were typically observed to segregate into two peaks; early arriving (latency, about 20-30 ms) and a later arriving SSEP (about 35-45 ms; FIGS. 13 B and 13C; FIGS. 14A and 14B). In the first experiment depicted in FIG. 13C, subsequent records were taken at approximately 30 minutes, 1 hour, 24 hours, and 4 days after PEG treatment. In the second experiment, subsequent measurements were made approximately 6-8 hours, 18-24 hours (data not shown), 3 days, 2 weeks, and 1 month following the delayed application of PEG. In all animals, the failure to record an SSEP following stimulation of the tibial nerve was further confirmed to be due to a lack of conduction through the injury by a control procedure carried out on the same animal, where the medial nerve of the forelimb was stimulated. In all cases, this produced a characteristic SSEP for this spinal circuit unaffected by the injury (FIGS. 13 A-13C; FIG. 14B). In this investigation, sham-treated animals never regained the ability to conduct SSEPs through the injury site.

In the first experiment depicted in FIGS. 13B and 13C, a detectable SSEP was recorded within a few minutes after PEG application. Quantitative evaluation of 10 of these animal's electrical records showed that SSEP amplitudes continued to improve—averaging about 40% of their preinjury level, and displaying more typical latencies with time (FIGS. 13C and 13D). Remarkably, within minutes of the spinal injury, the total loss of physiological functioning was reversed in 23 of 25 PEG-treated animals. In the two animals that did not immediately respond to PEG application, SSEP recovery was later observed at the 2 weeks time-point (FIG. 14C, Table 3). In the four animals whose recovered SSEPs were tested by reinjury, the second compression of the spinal cord at the original injury site completely eliminated recovered SSEPs, confirming these were conducted through the lesion. In 9 of 11 experimental animals, the delayed application of PEG (about 8 hours post injury) produced a detectable SSEP within 18 hours (FIG. 14C).

All 34 PEG-treated animals recovered SSEP conduction contrasted to the complete failure of all control guinea pigs to conduct evoked potentials through the lesion. Only 3 of 22 sham-treated animals recovered CTM function in both experiments, while 20 of 25 PEG-treated animals recovered variable amounts of CTM functioning which continued to improve with time (Table 2,3).

Summary of the Results

This report is the first to show that an immediate and brief application of a hydrophilic fusogen, polyethylene glycol, to the site of a severe compression injury to the adult guinea pig spinal cord in vivo results in an immediate recovery of nerve impulse conduction and a progressive recovery of behavioral functioning of the CTM reflex—a quantitative index of white matter integrity [Borgens, R. B., et al. (1990) *J. Comp. Neurol.* 296:634-653; Blight, A. R., et al. (1990) *J. Comp. Neurol.* 296:614-633; Borgens, R. B., et al. (1987) *Science* 238:366-369]. Furthermore, an 8 hour delay in this application still resulted in a similar recovery of these functions. In sharp contrast, sham-treated animals never recovered the ability to conduct nerve impulses, and the minor occurrence of spontaneous recovery of CTM function was rare compared to the PEG-treated group.

This report provides clear evidence of a behavioral recovery dependent on an identified neural circuit within the damaged mammalian central nervous system in response to this experimental treatment [Borgens, R. B. and Shi, R. (1999) *J. Faseb* (in press)]. Together with our previous reports [Shi, R.

and Borgens, R. B. (1999) *J. Neurophysiology* 81:2406-2414; Shi, R., et al. (1999) *J. of Neurotrauma* 16:727-738], this suggests molecular repair and fusion of nerve membranes as a novel treatment of severe trauma to both peripheral nervous system as well as central nervous system tissue.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method of treating a mammalian patient having suffered an injury to its spinal cord, said method comprising contacting the injured spinal cord after the injury but within a period no greater than about 24 hours after said injury with a composition comprising an effective amount of at least one C1-C10 polyalkylene glycol, wherein the effective amount of at least one C1-C10 polyalkylene glycol is effective to restore nerve impulse conduction through said injured spinal cord, and wherein the effective amount of at least one C1-C10 polyalkylene glycol is at least about 40% by weight in the composition.

2. The method according to claim 1 wherein said spinal cord is severed.

3. The method according to claim 1 wherein said spinal cord is crushed spinal cord.

4. The method according to claim 1 wherein said polyalkylene glycol is selected from the group consisting of polymethylene glycol, polyethylene glycol, polypropylene glycol, polybutylene glycol, polypentylene glycol, polyhexylene glycol, polyheptylene glycol, polyoctylene glycol, polynonylene glycol, polydecylene glycol and mixtures, thereof.

5. The method according to claim 4 wherein said polyalkylene glycol is administered to said patient in a pharmaceutically acceptable carrier.

6. The method according to claim 5 wherein said polyalkylene glycol is selected from the group consisting of polyethylene glycol, polypropylene glycol and mixtures thereof.

7. The method according to claim 1 wherein said polyalkylene glycol is polyethylene glycol.

8. The method according to claim 5 wherein said polyalkylene glycol is polyethylene glycol having a molecular weight ranging from about 40 daltons to about 3500 daltons.

9. The method according to claim 1, wherein said polyalkylene glycol is polyethylene glycol and wherein said method further comprises the step of contacting said injured spinal cord with a synergistic amount of 4-aminopyridine and within an effective time of contacting said spinal cord with said polyethylene glycol so as to produce a synergistic increase in restoration of nerve function and reflex behavior in said patient.

10. A method of treating a mammalian patient having suffered an injury to its spinal cord, said method comprising contacting the injured spinal cord after the injury but within a period no greater than about 24 hours after said injury with a composition comprising an effective amount of polyethylene glycol, wherein the effective amount of polyethylene glycol is effective to restore nerve impulse conduction through said injured spinal cord and wherein the effective amount of polyethylene glycol is at least about 40% by weight in the composition.

11. The method according to claim 10 wherein said polyethylene glycol has a molecular weight ranging from about 40 daltons to about 3500 daltons.

12. The method according to claim 10 further comprising the step of contacting said injured spinal cord with a potassium channel blocker in the form of 4-aminopyridine in an effective amount and within an effective time of contacting said spinal cord with said polyethylene glycol.

13. The method according to claim 12 wherein said polyethylene glycol has a molecular weight ranging from about 40 daltons to about 3500 daltons.

14. The method according to claim 1 or 10 wherein the restoration of nerve impulse conduction is evidenced by a detectable increase in conduction action potentials, observation of anatomical continuity, restoration of more than one spinal root level, or an increase in reflex behavior.

* * * * *